(12) United States Patent
Marsala

(10) Patent No.: US 10,980,566 B2
(45) Date of Patent: Apr. 20, 2021

(54) SUBPIAL DELIVERY SYSTEM AND METHODS OF USE

(71) Applicant: The Regents of the University of California, Oakland, CA (US)

(72) Inventor: Martin Marsala, Solana Beach, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 16/954,146

(22) PCT Filed: Jan. 10, 2020

(86) PCT No.: PCT/US2020/013059
§ 371 (c)(1),
(2) Date: Jun. 16, 2020

(87) PCT Pub. No.: WO2020/146718
PCT Pub. Date: Jul. 16, 2020

(65) Prior Publication Data
US 2020/0397467 A1    Dec. 24, 2020

Related U.S. Application Data

(60) Provisional application No. 62/790,616, filed on Jan. 10, 2019.

(51) Int. Cl.
*A61B 17/34* (2006.01)
*A61B 17/02* (2006.01)
(Continued)

(52) U.S. Cl.
CPC ...... *A61B 17/3401* (2013.01); *A61B 17/0206* (2013.01); *A61M 5/142* (2013.01);
(Continued)

(58) Field of Classification Search
CPC .................. A61M 5/142; A61M 5/178; A61M 2202/206; A61M 2210/1003;
(Continued)

(56) References Cited

U.S. PATENT DOCUMENTS 5,871,487 A * 2/1999 Warner .................. A61B 90/11
604/116
8,292,874 B2 10/2012 Stivland et al.
(Continued)

FOREIGN PATENT DOCUMENTS

CN 101528922 A 9/2009
CN 103328038 A 9/2013
(Continued)

OTHER PUBLICATIONS

PCT/US2020/013059 International Search Report and Written Opinion dated Apr. 1, 2020.
(Continued)

*Primary Examiner* — Jason E Flick
(74) *Attorney, Agent, or Firm* — Foley & Lardner LLP

(57) ABSTRACT

Delivery devices, systems, and methods related thereto may be used on patients for spinal delivery of cells, drugs, or vectors. The patient population may include patients with spinal traumatic injury, amyotrophic lateral sclerosis, multiple sclerosis, spinal ischemia, and other spinal neurodegenerative disorder that will require spinal cell, vector, or drug delivery.

29 Claims, 21 Drawing Sheets

(51) Int. Cl.
    A61M 5/178    (2006.01)
    A61M 5/142    (2006.01)
(52) U.S. Cl.
    CPC ....... *A61M 5/178* (2013.01); *A61M 2202/206* (2013.01); *A61M 2210/1003* (2013.01); *A61M 2250/00* (2013.01)
(58) Field of Classification Search
    CPC . A61M 2250/00; A61M 5/14; A61B 17/3401; A61B 17/0206; A61B 17/34; A61B 17/02
    See application file for complete search history.

(56) References Cited

U.S. PATENT DOCUMENTS

| | | |
|---|---|---|
| 9,827,109 B2 * | 11/2017 | Steinberg ............... A61B 34/30 |
| 10,688,285 B2 | 6/2020 | Marsala et al. |
| 2002/0042607 A1 | 4/2002 | Palmer et al. |
| 2002/0082390 A1 | 6/2002 | Friddle et al. |
| 2002/0095124 A1 | 7/2002 | Palasis et al. |
| 2003/0069398 A1 | 4/2003 | Rippmann et al. |
| 2003/0130577 A1 | 7/2003 | Purdy et al. |
| 2003/0195633 A1 | 10/2003 | Hyde, Jr. |
| 2005/0085790 A1 | 4/2005 | Guest et al. |
| 2006/0205999 A1 | 9/2006 | Berger et al. |
| 2007/0142748 A1 | 6/2007 | Deshmukh et al. |
| 2008/0051357 A1 | 2/2008 | Chang |
| 2008/0154262 A1 | 6/2008 | Brundobler et al. |
| 2010/0004625 A1 | 1/2010 | Boulis |
| 2010/0023021 A1 | 1/2010 | Flaherty |
| 2010/0030184 A1 * | 2/2010 | Boulis ................. A61B 17/3472 604/500 |
| 2010/0198189 A1 | 8/2010 | Marsala |
| 2012/0221063 A1 * | 8/2012 | Abdou .................. A61F 2/4611 606/86 A |
| 2013/0211380 A1 | 8/2013 | Aquino et al. |
| 2014/0058357 A1 | 2/2014 | Keyser et al. |
| 2014/0073684 A1 | 3/2014 | Stoffel et al. |
| 2014/0256801 A1 | 9/2014 | Glorioso et al. |
| 2015/0224331 A1 | 8/2015 | Marsala |
| 2015/0343038 A1 | 12/2015 | Marsala |
| 2016/0081956 A1 | 3/2016 | Kaufman et al. |
| 2018/0008727 A1 | 1/2018 | Marsala |
| 2018/0117282 A1 | 5/2018 | Marsala et al. |
| 2019/0071486 A1 | 3/2019 | Marsala |

FOREIGN PATENT DOCUMENTS

| | | |
|---|---|---|
| WO | 1994/10988 A | 5/1994 |
| WO | 2004/060464 A2 | 7/2004 |
| WO | WO-2006/047554 | 5/2006 |
| WO | WO-2008/112177 | 9/2008 |
| WO | 2010/071832 A1 | 6/2010 |
| WO | 2011/057171 A1 | 5/2011 |
| WO | 2012/075337 A2 | 6/2012 |
| WO | 2014/047540 A1 | 3/2014 |
| WO | 2014/116652 A2 | 7/2014 |
| WO | 2014/184576 A2 | 11/2014 |
| WO | 2016/122791 A1 | 8/2016 |
| WO | 2017/172606 A1 | 10/2017 |

OTHER PUBLICATIONS

Chaudhry et al. "The Vesicular GABA Transporter, VGAT, Localizes to Synaptic Vesicles in Sets of Glycinergic as Well as GABAergic Neurons," The Journal of Neuroscience, Dec. 1, 1998, 18(23):9733-9750.
Poston et al. "Catheter delivery systems for infusions into the cortex," Journal of Medical Engineering & Technology, Jul. 2011, 35(5):246-253.
Kantor et al. "Clinical Applications Involving CNS Gene Transfer," Adv Genet., 2014, 87:71-124.
Bouard et al. "Viral vectors: from virology to transgene expression," British Journal of Pharmacology, 2009, 157:153-165.
Adkins et al. "Tiagabine: A Review of its Pharmacodynamic and Pharmacokinetic Properties and Therapeutic Potential in the Management of Epilepsy," Drugs, Mar. 1998, 55(3):437-460.
Gholizadeh et al. "Transduction of the Central Nervous System After Intracerebroventricular Injection of Adeno-Associated Viral Vectors in Neonatal and Juvenile Mice," Human Gene Therapy Methods, Aug. 2013, 24:205-213.
EP14742941 Extended European Search Report dated Jun. 20, 2016.
Dayton et al. "The advent of AAV9 expands applications for brain and spinal cord gene delivery," Expert Opinion on Biological Therapy, Jun. 15, 2012, 12(6):757-766.
Federici et al. "Robust spinal motor neuron transduction following intrathecal delivery of AAV9 in pigs," Gene Therapy, 2012, 19(8):852-859.
Foust et al. "Intravascular AAV9 preferentially targets neonatal neurons and adult astrocytes," Nature Biotechnology, Jan. 2009, 27(1):59-65.
Hirai et al. "Intrathecal shRNA-AAV9 Inhibits Target Protein Expression in the Spinal Cord and Dorsal Root Ganglia of Adult Mice," Human Gene Therapy Methods, Apr. 1, 2012, 23(2):119-127.
Kakinohana et al. "Combinational Spinal GAD65 Gene Delivery and Systemic GABA-Mimetic Treatment for Modulation of Spasticity," PLOS ONE, Jan. 2012, 7(1):e30561.
PCT/US2017/024285 International Search Report and Written Opinion dated Aug. 10, 2017.
Jin et al. "Demonstration of Functional Coupling between Gamma-Aminobutyric acid (GABA) Synthesis and Vesicular GABA Transport into Synaptic Vesicles," Proc Natl Acad Sci USA, Apr. 2003, 100(7):4293-4298.
EP15880645 Extended European Search Report dated May 24, 2018.
Colak et al. "Adenovirus-mediated gene therapy for experimental spinal cord tumors: tumoricidal efficacy and functional outcome," Brain Research, May 1995, 691:76-82.
JP2017-540569 Office Action dated Jun. 26, 2018.
PCT/US2015/065704 International Search Report dated Feb. 25, 2016.
CN201580078566.9 Office Action dated Sep. 24, 2019.
JP2017-540569 Office Action dated Jun. 4, 2019.
Bell et al. "Motor Neuron Transduction After Intracisternal Delivery of AAV9 in a Cynomolgus Macaque," Human Gene Therapy Methods, Apr. 2015, 26:43-44.
Duque et al. "Intravenous Administration of Self-complementary AAV9 Enables Transgene Delivery to Adult Motor Neurons," Molecular Therapy, Jul. 2009, 17(7):1187-1196.
Foust et al. "Therapeutic AAV9-mediated Suppression of Mutant SOD1 Slows Disease Progression and Extends Survival in Models of Inherited ALS," Molecular Therapy, Dec. 2013, 21(12):2148-2159.
Gray et al. "Preclinical Differences of Intravascular AAV9 Delivery to Neurons and Glia: A Comparative Study of Adult Mice and Nonhuman Primates," Molecular Therapy, Jun. 2011, 19(6):1058-1069.
Kakinohana et al. "Region-specific cell grafting into cervical and lumbar spinal cord in rat: a qualitative and quantitative stereological study," Experimental Neurology, 2004, 190:122-132.
Meyer et al. "Improving Single Injection CSF Delivery of AAV9-mediated Gene Therapy for SMA: A Dose-response Study in Mice and Nonhuman Primates," Molecular Therapy, Mar. 2015, 23(3):477-487.
Passini et al. "Translational Fidelity of Intrathecal Delivery of Self-Complementary AAV9-Survival Motor Neuron 1 for Spinal Muscular Atrophy," Human Gene Therapy, Jul. 2014, 25:619-630.
Usvald et al. "Analysis of Dosing Regimen and Reproducibility of Intraspinal Grafting of Human Spinal Stem Cells in Immunosuppressed Minipigs," Cell Transplantation, 2010, 19:1103-1122.
Xiao et al. "Production of High-Titer Recombinant Adeno-Associated Virus Vectors in the Absence of Helper Adenovirus," Journal of Virology, Mar. 1998, 72(3):2224-2232.

(56) References Cited

OTHER PUBLICATIONS

Xu et al. In Vivo Gene Knockdown in Rat Dorsal Root Ganglia Mediated by Self-Complementary Adeno-Associated Virus Serotype 5 Following Intrathecal Delivery, PLoS ONE, Mar. 2012, 7(3):e32581.
CN201580078566.9 Office Action dated Apr. 28, 2020.
EP17776384.4 Extended European Search Report dated Jul. 31, 2019.
Kitzman, Patrick. "Changes in vesicular glutamate transporter 2, vesicular GABA transporter and vesicular acetylcholine transporter labeling of sacrocaudal motoneurons in the spastic rat," Experimental Neurology, 2006, 197:407-419.
Bu et al. "Two human glutamate decarboxylases, 65-kDa GAD and 67-kDa GAD, are each encoded by a single gene," Proc. Natl. Acad. Sci. USA, Mar. 1992, 89:2115-2119.
"H.sapiens mRNA for glutamate decarboxylase, GenBank: X69936. 1," GenBank, Mar. 16, 1993 [Retrieved from the Internet: https://www.ncbi.nlm.nih.gov/nuccore/X69936].
PCT/US2018/049914 International Search Report and Written Opinion dated Nov. 21, 2018.

\* cited by examiner

SUBPIAL DELIVERY SYSTEM AND METHODS OF USE

CROSS REFERENCE TO RELATED APPLICATION

This application is a US national phase application under 35 U.S.C. § 371 of international patent application no. PCT/US2020/013059, filed Jan. 10, 2020, which claims the benefit of priority under 35 U.S.C. § 119(e) of U.S. Ser. No. 62/790,616, filed Jan. 10, 2019, the entire content of each of which is incorporated herein by reference.

BACKGROUND OF THE INVENTION

Field of the Invention

The invention relates generally to a surgical device and, more specifically, to a system that permits delivery of soluble substances, gene vectors, or cell suspensions into the spinal subpial space of a subject.

Background Information

The spinal cord is a delicate structure that rests within the spinal canal and is surrounded and protected by the bony structure of the spinal column composed of vertebrae. Within the spinal canal, the spinal cord is surrounded by three layers of fibrous membranes called meninges. The outermost meningeal membrane is called dura mater, the intermediate membrane is called arachnoid mater, and the innermost membrane, laying on the surface of the spinal cord, is called pia mater. The space between the arachnoid membrane and spinal cord is called the intrathecal (or subarachnoid) space. Cerebrospinal fluid (CSF) surrounds the spinal cord and flows from the brain, down the spinal canal, and back up to the brain in intrathecal space. Normally, the spinal cord ends at about the first or second lumbar vertebrae in the adult human. All peripheral nerves responsible for movement and sensation of the arms, legs, and torso originate from the spinal cord.

Intrathecal injections of drugs have been used for spinal anesthesia, chemotherapy, pain management applications, and for taking samples of cerebral spinal fluid. Administering a substance to the intrathecal space surrounding the spinal cord is often performed in order to avoid the blood-brain barrier and to achieve a higher concentration of drugs in deep spinal parenchyma. A direct intraspinal-intraparenchymal grafting of human neural stem cells is currently being tested as a therapeutic approach for treatment of amyotrophic lateral sclerosis and spinal trauma-induced paralysis.

Currently existing clinically-approved injection devices or spinal needles, which are being used for epidural or intrathecal drug delivery, CSF sampling into/from spinal intrathecal space or for direct spinal parenchymal injections (as used for cell delivery), do not permit a safe and multi-segmental subpial delivery of soluble substances or cell suspensions. Therefore, a need exists for a device that permits safe multi-segmental subpial delivery of such soluble substances or cell suspensions.

SUMMARY OF THE INVENTION

The present invention is based on development of a subpial delivery system that permits the delivery of soluble substances (e.g., drugs), gene or RNA vectors (e.g., AAV9, HIV1, microRNA (miRNA), small hairpin RNA (shRNA), or antisense oligonucleotide (ASO)), or cell suspensions into a surgical site, such as a spinal subpial space of a subject. Accordingly, the invention provides a subpial delivery system. The system includes (a) a platform having (i) a frame having a top surface, a bottom surface, and an axis, the frame comprising an aperture defining a surgical site, (ii) a rail fixedly attached to the top surface of the frame and positioned perpendicular to the axis, (iii) a retractor moveably attached to the top surface of the frame and configured to move in a direction perpendicular to the axis, and (iv) an anchor moveably attached to the frame and configured to engage a bone within the surgical site so as to secure the platform over the surgical site; (b) a manipulator moveably attached to the rail of the platform, the manipulator having (i) a post having a central axis and extending in a direction perpendicular to the top surface of the frame, (ii) a crossmember moveably attached to a distal portion of the post and positioned parallel to the top surface of the frame, and (iii) a coupler moveably attached to the crossmember, the coupler comprising a threaded portion configured for removable attachment to a needle assembly; (c) a needle assembly removably attached to the coupler, the needle assembly including (i) an elongated body having an axis and a lumen disposed therethrough, (ii) a fastener disposed on distal end portion of the elongated body, the fastener being configured to engage the threaded portion of the coupler, and (iii) a needle. The needle includes (a) an elongated shaft disposed within the first lumen of the elongated body, the elongated shaft defining a second lumen and having a proximal end portion comprising an upper section substantially parallel to the axis of the elongated body, a middle section angled away from the axis of the elongated body, and a lower section angled toward the axis of the elongated body, such that the lower section is substantially perpendicular to the axis of the elongated body, (b) a point disposed at the proximal end of the elongated shaft such that the point is positioned in alignment with the axis of the elongated body, and (c) an opening disposed within the substantially parallel section of the elongated body, wherein the opening is in fluid communication with the second lumen of the elongated body, and (d) a reservoir fixedly attached to a distal end of the elongated shaft of the needle assembly and disposed in fluid communication with the lumen of the elongated body, the reservoir being configured for containing a substrate prior to delivery of the substrate through the opening of the needle.

In various embodiments, the frame includes a pair of retractors, each retractor being attached to the top surface of the frame at opposing sides of the surgical site. In various embodiments, the frame includes a pair of anchors, each anchor being attached to the frame at opposing sides of the surgical site. In various embodiments, the frame further includes a pair of bars fixedly attached to the top surface and positioned perpendicular to the axis of the frame, wherein each bar is located outside of the surgical site defined by the lumen, and wherein each anchor is movably mounted to each bar via a mount. In various embodiments, the frame includes a pair of anchors, each anchor being attached to the frame on the same side of the surgical site. In various embodiments, the frame further includes a pair of sleeves fixedly attached to the frame and configured for movable attachment to the anchors. In various embodiments, the anchor includes a pair of serrated jaws disposed at a proximal end thereof, the pair of serrated jaws being hingedly attached to one another and configured to clamp onto a bone within the surgical site. In various embodiments, the anchor includes a hook disposed at a proximal end, the hook being configured to engage a bone within the surgical site.

The manipulator may further include a base disposed at a proximal end of the post thereof, the base being configured for frictional attachment to the rail of the frame. In various embodiments, the manipulator further includes a pivotal joint disposed along the post, the pivotal joint being configured to allow the distal portion of the post to pivot in a direction away from the central axis thereof. In various embodiments, the manipulator further includes a first knob disposed at a distal end of the post, the first knob being configured to lock the pivotal joint of the post in a preselected position. In various embodiments, the crossmember further includes a second knob, the second knob being configured to lock the coupler in a preselected position.

The coupler may further include an arm having a first end slidingly disposed within the crossmember and the threaded portion disposed at a second end, and a slot disposed in the threaded portion and traversing the second end of the coupler, the slot being configured to accept the elongated body of the needle assembly. In various embodiments, the arm further includes a rotatable joint configured to adjust the angle of the slot and threaded portion relative to the central axis of the post. In various embodiments, the arm further includes a knob configured to lock the rotatable joint in a preselected position.

The opening of the needle may therefore be located in a position facing toward the surgical site. In various embodiments, the needle assembly further includes a fluid fitting disposed at a distal end of the elongated body and configured to provide removable attachment between the needle assembly and the reservoir. In various embodiments, the fluid fitting includes a body having a lumen sized and shaped to accept the distal end of the elongated shaft of the needle, wherein the distal end of the elongated shaft and the proximal end of the reservoir are separated by a space.

In various embodiments, the reservoir is formed from tubing. In various embodiments, the reservoir further includes a syringe disposed at a distal end of the tubing and configured to supply the substrate to the reservoir. In various embodiments, the subpial delivery system further includes a pump attached to the tubing, the pump being configured to pump the substrate from the reservoir through the opening of the needle. In various embodiments, the substrate is selected from the group consisting of soluble substances, cells, vectors, drugs, viruses, plasmids, and growth factors.

In another aspect, the invention provides a method for delivering a substrate to the subpial space of a subject. The method includes exposing a spinal cord of the subject; positioning and securing the subpial delivery system over the exposed spinal cord thereby creating a surgical site; loading a substrate to be delivered to the subpial space into the reservoir; inserting the point of the needle towards the spinal cord (into the subpial space) in a direction substantially parallel to the spinal cord, thereby creating a pial opening site of the subpial space; and delivering a dose of the substrate to the spinal cord. In various embodiments, the method includes adjusting the needle assembly using the manipulator prior to the step of inserting such that the lower section is substantially parallel to the spinal cord of the subject.

In various embodiments, the step of loading includes disconnecting a fluid fitting disposed at a distal end of the elongated body of the needle assembly; flowing the substrate into the reservoir; and reconnecting the reservoir to the needle assembly. In various embodiments, the method further includes priming the subpial delivery system prior to the step of inserting by flowing substrate from the reservoir through the opening of the needle. In various embodiments, the step of delivering includes activating a pump attached to the reservoir, the pump being configured to control flow of the substrate the reservoir through the opening of the needle. In various embodiments, the step of delivering includes actuating a syringe attached to a distal end of the reservoir, the syringe being configured to control flow of the substrate the reservoir through the opening of the needle. In various embodiments, the method includes performing a laminectomy on the subject prior to the step of positioning and securing.

BRIEF DESCRIPTION OF THE DRAWINGS

Embodiments of the present invention and their advantages are best understood by referring to the detailed description that follows. It should be appreciated that like reference numerals are used to identify like elements illustrated in one or more of the figures.

DETAILED DESCRIPTION OF THE INVENTION

Figure 1:
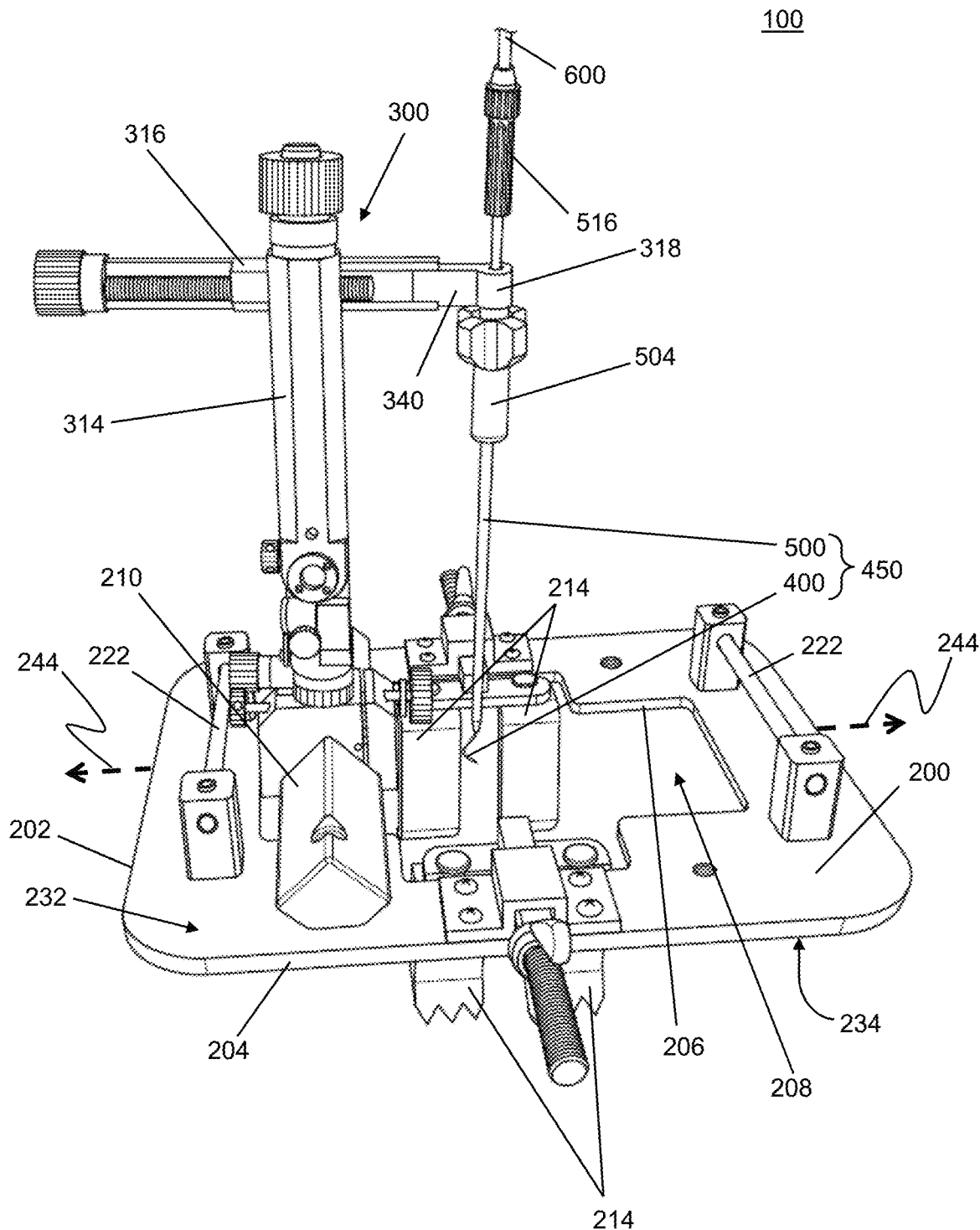
FIG. 1 is a pictorial diagram showing a perspective view of an exemplary embodiment of the subpial delivery system.

The present invention is based on development of a subpial delivery system that permits the delivery of soluble substances (e.g., drugs), gene or RNA vectors (e.g., AAV9, HIV1, microRNA (miRNA), small hairpin RNA (shRNA)), or cell suspensions into the spinal subpial space of a subject. More specifically, the subpial delivery system incorporates a needle having multiple bends that is designed for accuracy and precision in reaching a targeted spinal subpial location of small animal species, large animal species, and humans (e.g., a patient).

Before the present systems, methods and devices are described, it is to be understood that this invention is not limited to the particular configurations, methods, and experimental conditions described, as such configurations, methods, and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure and so forth.

The term "comprising," which is used interchangeably with "including," "containing," or "characterized by," is inclusive or open-ended language and does not exclude additional, unrecited elements or method steps. The phrase "consisting of" excludes any element, step, or ingredient not specified in the claim. The phrase "consisting essentially of" limits the scope of a claim to the specified materials or steps and those that do not materially affect the basic and novel characteristics of the claimed invention. The present disclosure contemplates embodiments of the invention compositions and methods corresponding to the scope of each of these phrases. Thus, a composition or method comprising recited elements or steps contemplates particular embodiments in which the composition or method consists essentially of or consists of those elements or steps.

As used herein, the term "dorsoventral" or "dorso-ventral" is an adjective that refers to extending along or denoting an axis joining the dorsal and ventral surfaces of a subject. Included in the term is extending from the back to the belly of the animal.

As used herein, the term "laminectomy" refers to a surgical procedure that removes a portion of the vertebral bone called the lamina, which is the roof of the spinal canal. Likewise, the term "laminoplasty" refers to a surgical procedure that is typically used for treating spinal stenosis by relieving pressure on the spinal cord. Such techniques are typically used for expanding the spinal canal of a subject to relieve pressure on the spinal cord or nerves by reconstruction of the laminar arch or partial or complete removal of the lamina. Without being bound by theory, one difference between the two procedures is the amount of bone and/or muscle tissue removed from the subject.

As used herein, the terms "stereotaxis," "stereotaxic," and "stereotactic" are used interchangeably to refer to methods in neurosurgery and neurological research for locating points within the brain or spinal cord using an external, three-dimensional frame of reference usually based on the Cartesian coordinate system. Methods of stereotactic surgery are known in the art.

The term "subject" as used herein refers to any individual or patient to which the subject methods are performed. Generally the subject is human, although as will be appreciated by those in the art, the subject may be an animal. Thus other animals, including mammals such as rodents (including mice, rats, hamsters, and guinea pigs), cats, dogs, rabbits, farm animals including cows, horses, goats, sheep, pigs, etc., and primates (including monkeys, chimpanzees, orangutans, and gorillas) are included within the definition of subject.

The term "substrate" refers to any injectable substance, including but not limited to cells, drugs, viruses, plasmids, growth factors and the like. The substrate may take any suitable form of matter, including a liquid, a suspension, a gel, an encapsulated solid, a nanoparticle suspension, a slow- or extended-release polymer composition and the like.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described.

Figure 7:
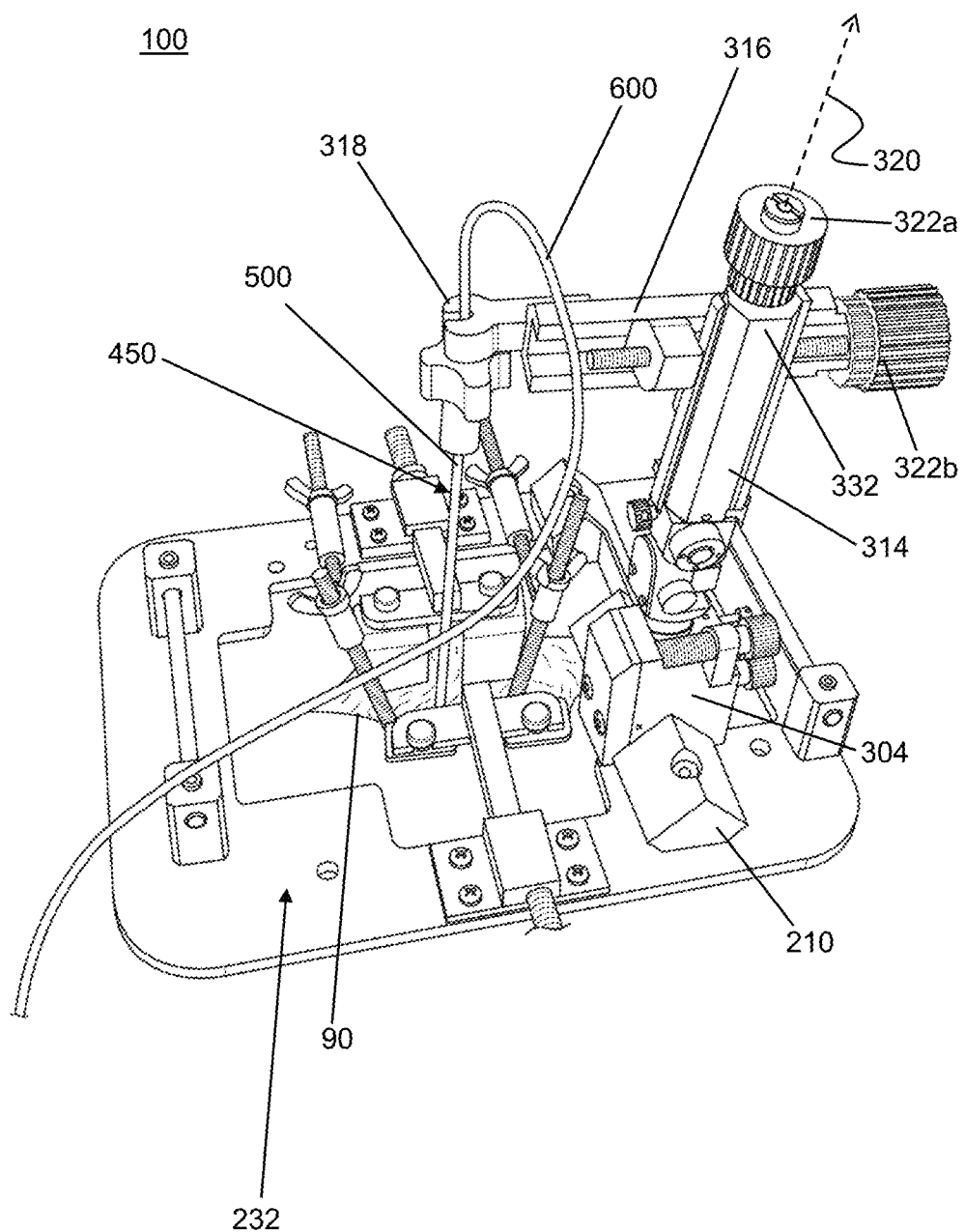
FIG. 7 is a pictorial diagram showing a perspective view of an exemplary manipulator and reservoir of the subpial delivery system.

Referring now to FIGS. 1-3 and 7, the invention provides a subpial delivery system 100 that includes a platform 200, a manipulator 300 mounted to the platform 200, a needle assembly 450 attached to the manipulator 300, and a reservoir 600 (shown in FIG. 7).

As shown in FIGS. 4-7, platform 200 includes a frame 202 having a top surface 232, a bottom surface 234 and an aperture 208 disposed along an axis 244 therethrough. In use, the aperture 208 defines a surgical site 90 (e.g., an incision of a laminectomy) of a subject in need of a subpial injection. Fixedly attached to the top surface 232 of the frame 202 is a rail 210, which is positioned perpendicular to the axis 244 of the frame 202. One or more retractors 214 are movably attached to the top surface 232 of frame 202, each retractor 214 being configured to move in a direction perpendicular to axis 244. In various embodiments, each retractor 214 may be slidingly disposed within a mounting bracket 240 that is fixedly attached to the top surface 232 of the frame 202. As such, the one or more retractors 214 may be inserted along the lateral edges of the surgical site and used to pull multiple layers of tissue away from axis 244 to further expose surgical site 90.

Figure 5:
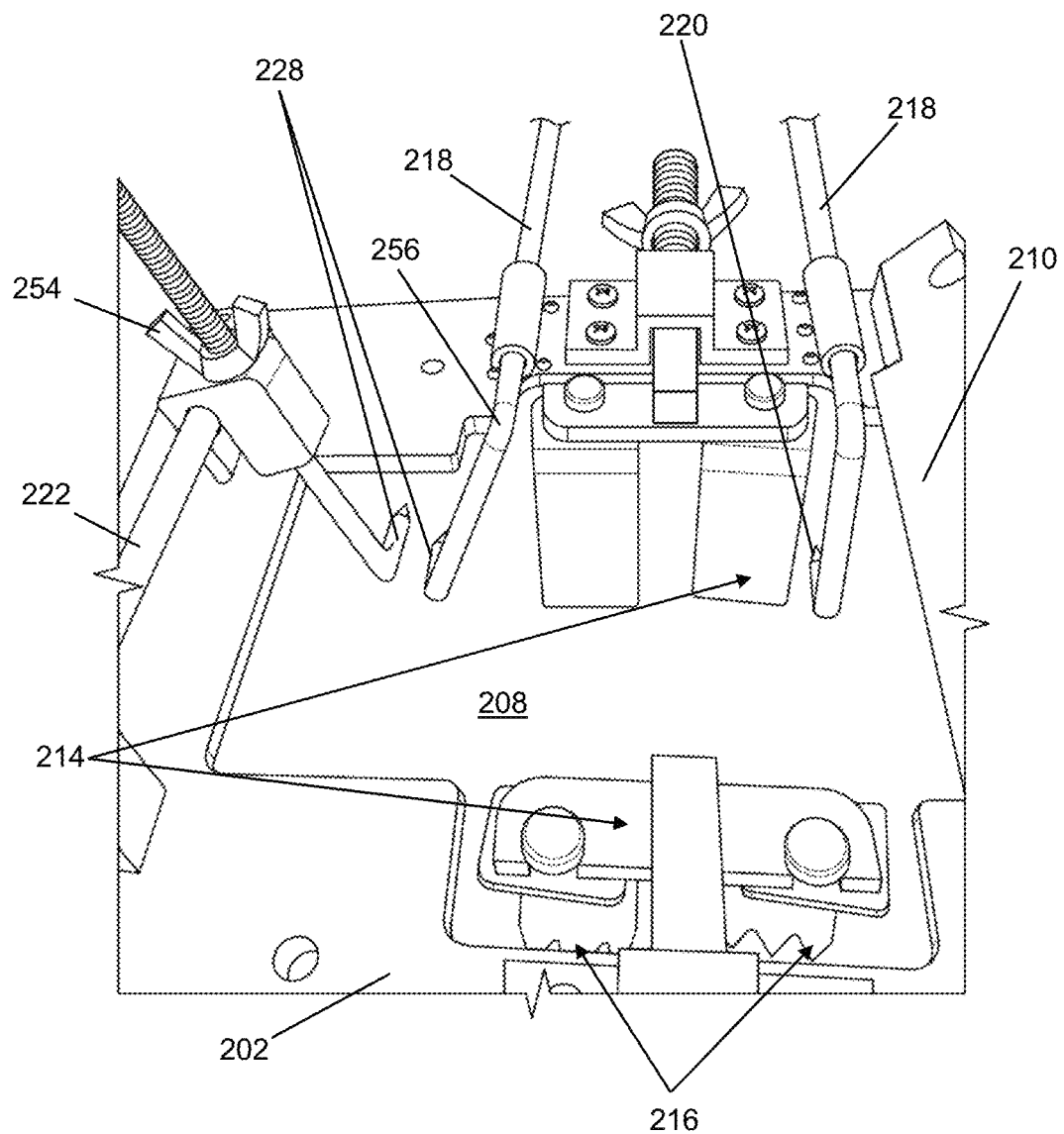
FIG. 5 is a pictorial diagram showing a perspective view of an exemplary embodiment of the platform of the subpial delivery system showing anchors, retractors and the surgical site.
Figure 16:
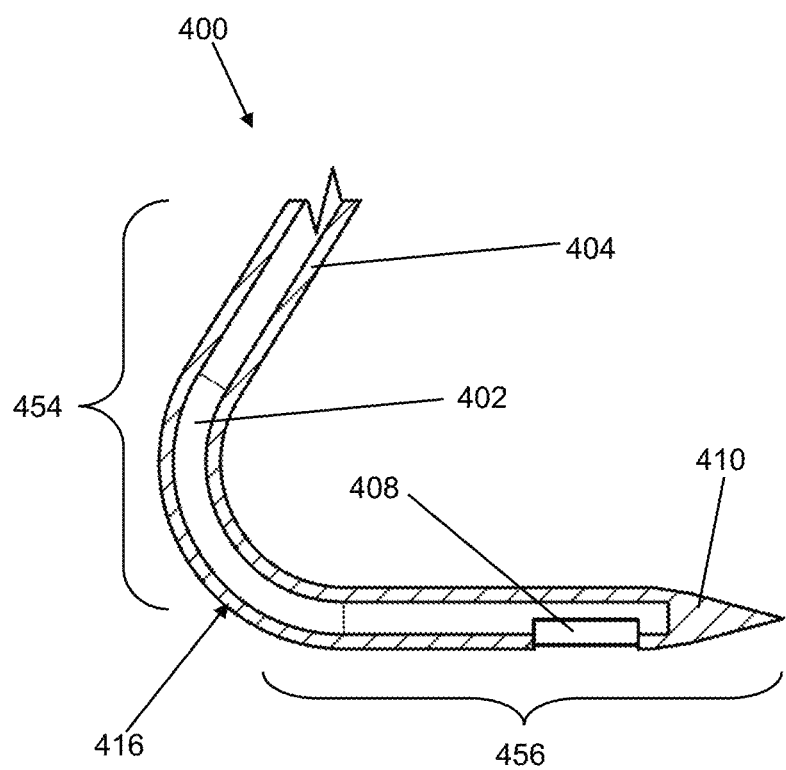
FIG. 16 is a pictorial diagram showing a partial cross-sectional view of an exemplary needle of the subpial delivery system.

In various embodiments, retractors 214 may be moveably and/or slidingly attached to top surface 232 of frame 202 on opposing sides of surgical site 90 (i.e., opposing sides of aperture 208). In use, retractors 214 may be inserted into an incision of surgical site 90 and traversed outward (i.e., moved away from axis 244 and toward inner perimeter 206) by a user (e.g., a surgeon) to pull tissue and paravertebral muscle away from surgical site 90, thereby improving visibility and access to secure platform 200 to the surgical site 90 (see FIG. 7). In an exemplary embodiment, retractors 214 may be traversed fore and aft relative to axis 244 by rotation of a wing nut 250 on a threaded shaft 248 of retractors 214. In various embodiments, retractors 214 may have sawtoothed or pronged ends, as shown in FIGS. 5 and 16, respectively, to grip surrounding tissue of surgical site 90.

Figure 18:
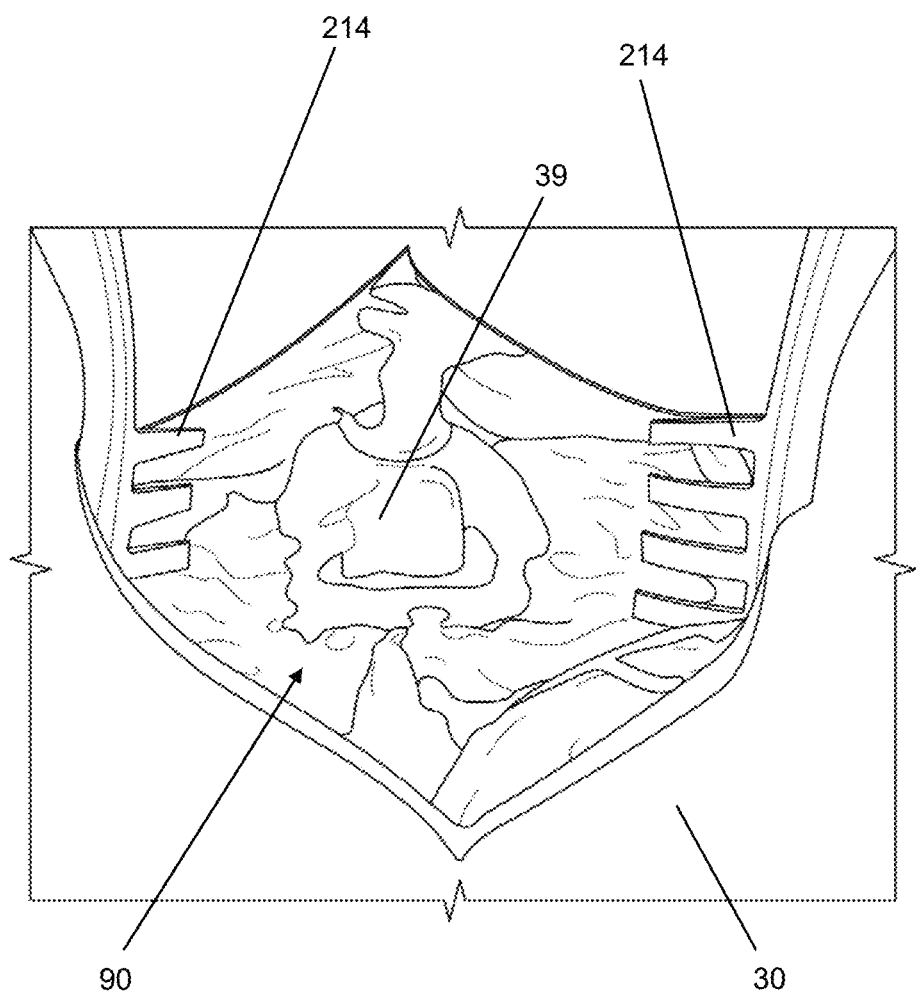
FIG. 18 is a pictorial diagram showing an exemplary surgical site opened by retractors of the subpial delivery system.
Figure 19:
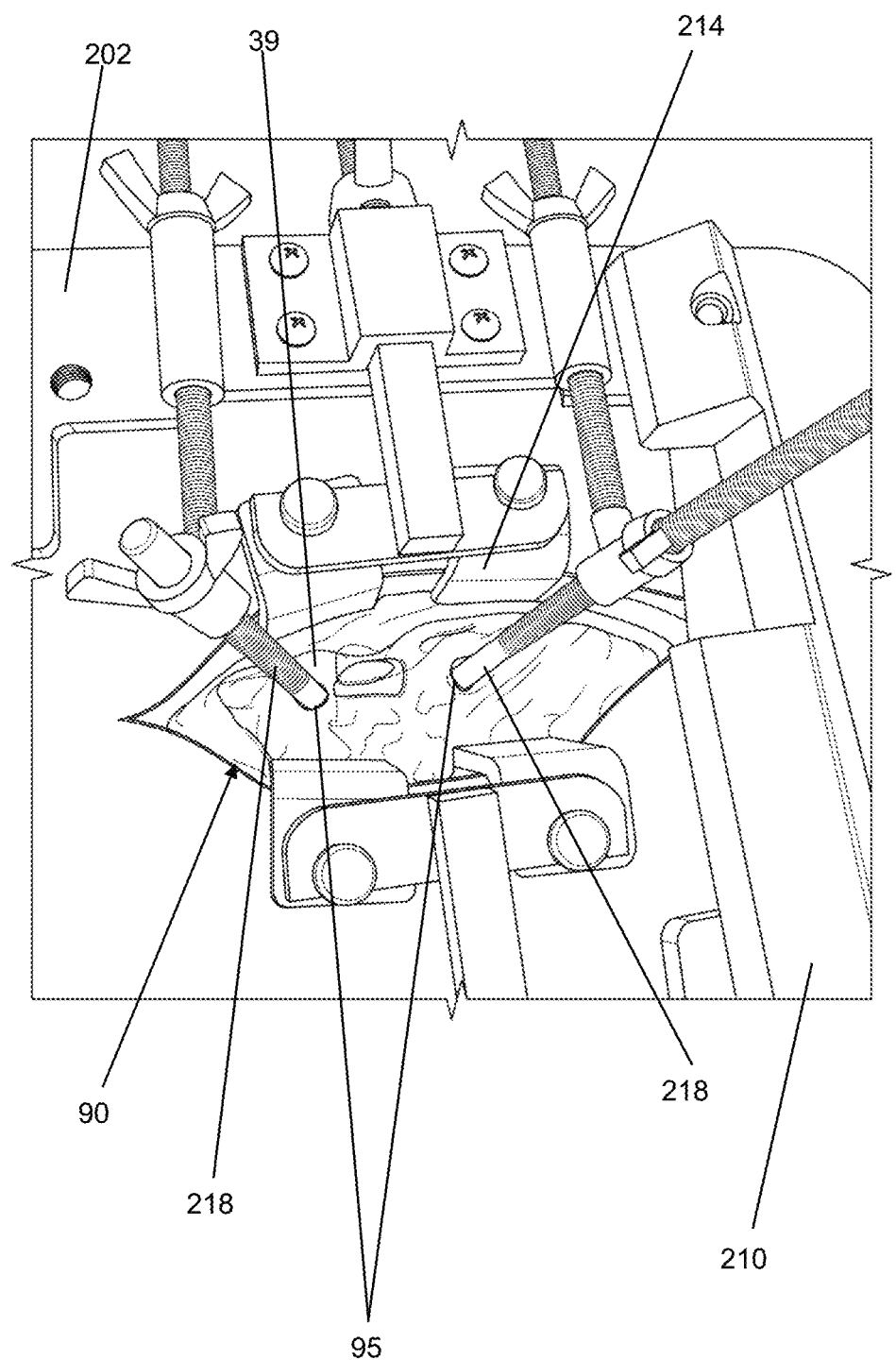
FIG. 19 is a pictorial diagram showing attachment of an exemplary embodiment of the platform of the subpial delivery system to a bone within the surgical site of a subject.
Figure 20:
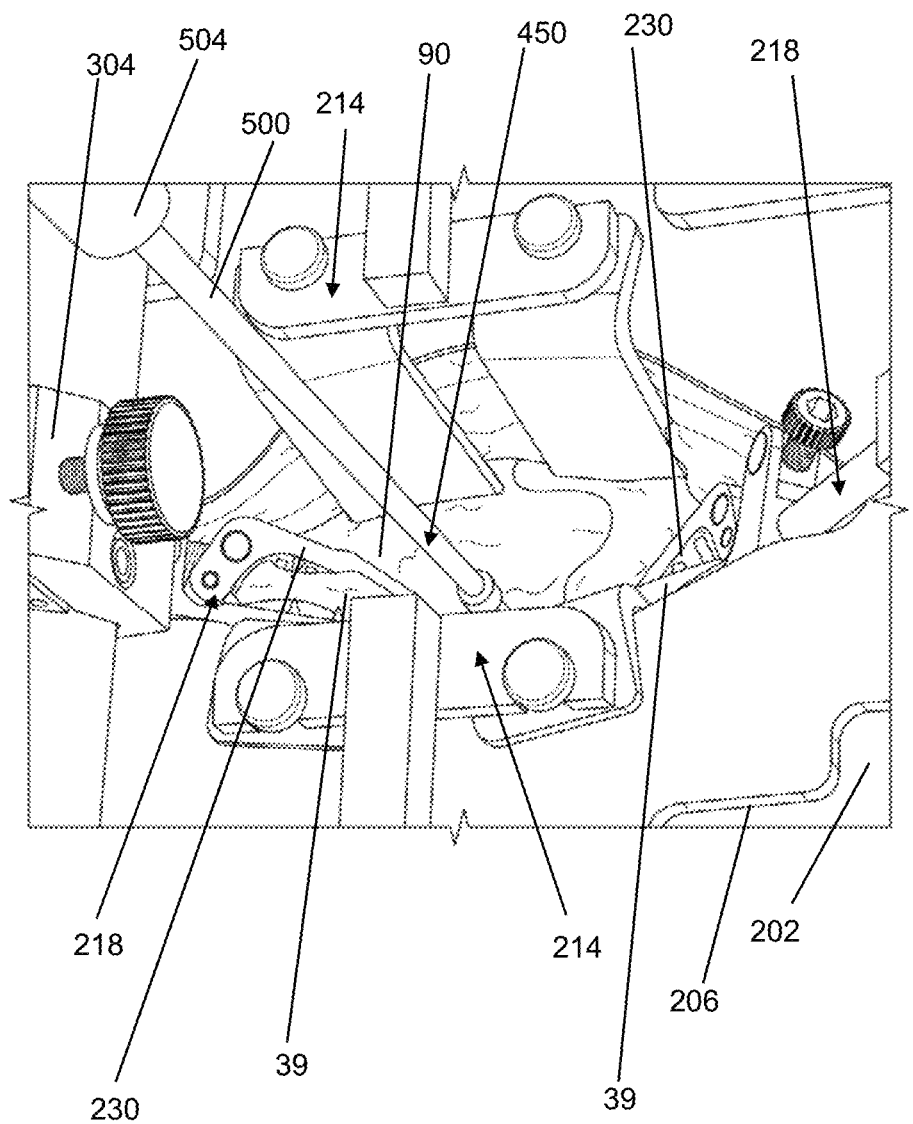
FIG. 20 is a pictorial diagram showing the positioning of the needle assembly in a surgical site in accordance with one or more embodiments with the present disclosure.
Figure 21:
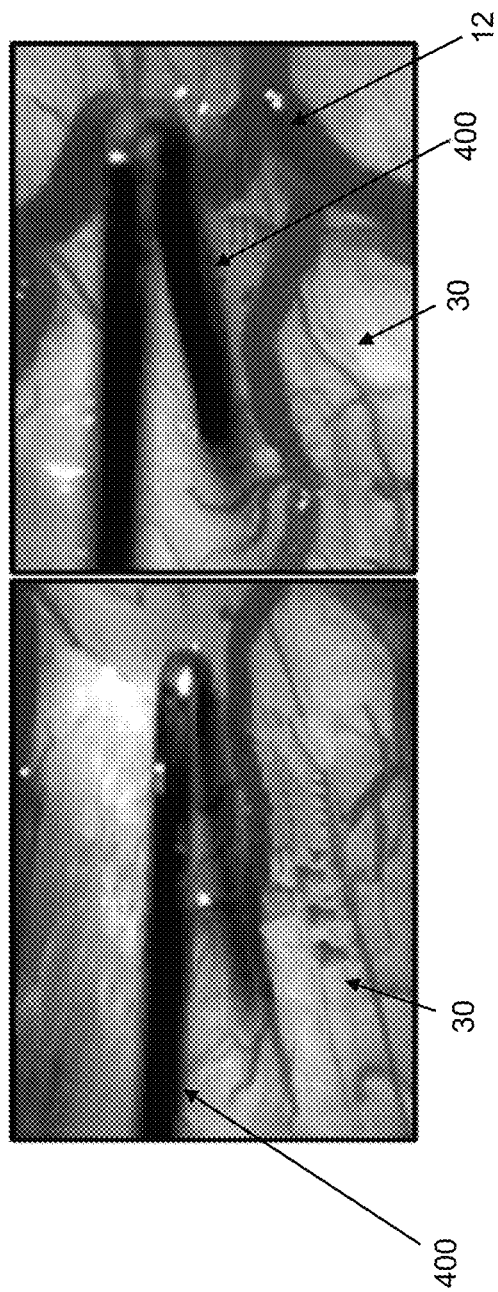
FIG. 21 is a series of pictorial diagrams showing insertion of the needle into the subpial space using the subpial delivery system and delivering substrate thereto.

Moveably attached to the frame 202 is one or more anchors 218, each anchor 218 being configured to engage a bone 39 (e.g., vertebra, see FIG. 18) within the surgical site 90 so as to secure the platform 200 to the subject (e.g., platform 200 will move in concert with any minor movements of the subject such that platform 200 remains in a fixed position relative to the surgical site 90). In various embodiments, anchors 218 may be moveably and/or slidingly attached to frame 202 at various locations. For example, anchors 218 may be disposed on opposing sides of surgical site 90 (i.e., opposing sides of aperture 208). In another example, anchors 218 may be positioned on the same side (e.g., on same side of aperture 208) or adjacent sides of surgical site 90. Anchors 218 may be attached to frame 202 using one or more sleeves 236 or bars 222, alone or in combination. In various embodiments, one or more sleeves 236 are fixedly attached to top surface 232 of frame 202, each sleeve being configured for movable attachment to anchors 218. For example, frame 202 may include a pair of sleeves 236 through which anchors 218 are inserted to allow for rotatable movement of the anchors 218 along with transverse movement of the anchors 218 relative to the surgical site 90 (e.g., in a direction perpendicular to axis 244). Anchors 208 may further include, for example, wing nuts 254 to facilitate transverse movement and secure engagement to a bone 39 within the surgical site 90 so as to secure the platform 200 over the surgical site 90. Sleeves 236 may be located on opposing sides of retractor 214 (as shown in FIG. 4) or may be located on opposing sides of the surgical site (not shown).

The engaging portion of anchor 218 may be formed into various shapes, such as a hook 228 or a clamp 230. Thus, in various embodiments, anchor 218 includes a hook 228 disposed at a proximal end 256 thereof, the hook 228 being configured to engage a bone 39 within surgical site 90. More specifically, the hook 228 includes a pointed end 220 that may engage a predrilled hole 95 or a protrusion of bone 39 within surgical site 90 to secure platform 200 in place over surgical site 90. Pointed end 220 may be angled (e.g., a 90-degree angle) such that pointed end 220 faces a direction perpendicular to axis 244 and parallel to top surface 232 of frame 202. However, in another exemplary embodiment, the anchor 218 includes a clamp 230, which includes a pair of serrated jaws 246 disposed at a proximal end of anchor 218. Serrated jaws 246 are hingedly attached to one another and configured to clamp onto a bone 39 within the surgical site 90. Serrated jaws 246 may be locked into position using, for example, a rotatable knob or a coil spring that provides resistance. In various embodiments, anchors 218 may be monolithic (i.e., each anchor 218 may be formed from a rod of stainless steel or titanium that is bent into a desired shape (as shown in FIG. 4). In various embodiments, anchors 218 may further include a threaded rod with a tubular sleeve at the end that allows for a second rod to be adjustably threaded therein and secured in a desired position (see FIG. 5).

Figure 2:
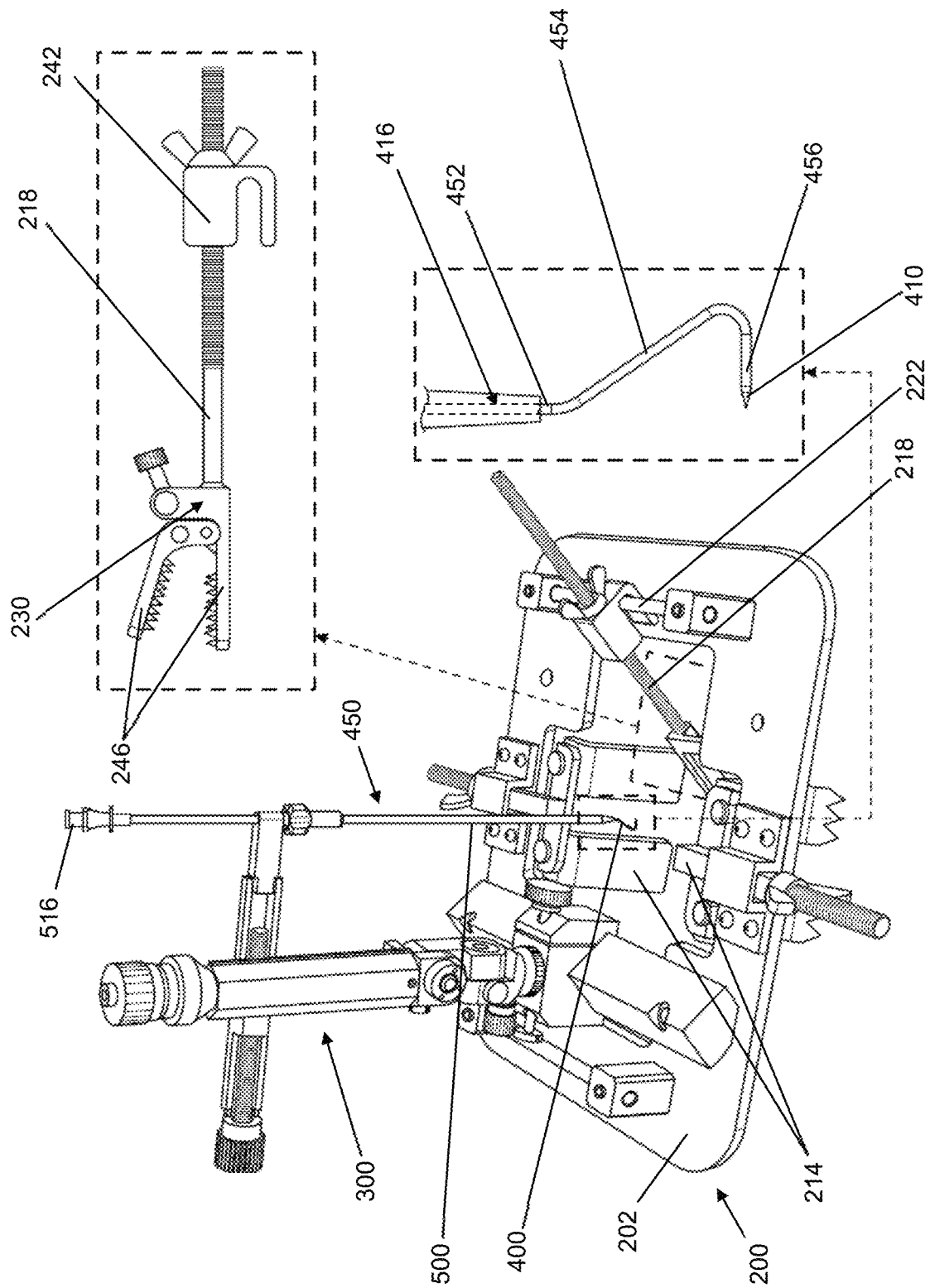
FIG. 2 is a pictorial diagram showing a perspective view of an exemplary embodiment of the subpial delivery system along with views of an anchor and the needle.
Figure 3:
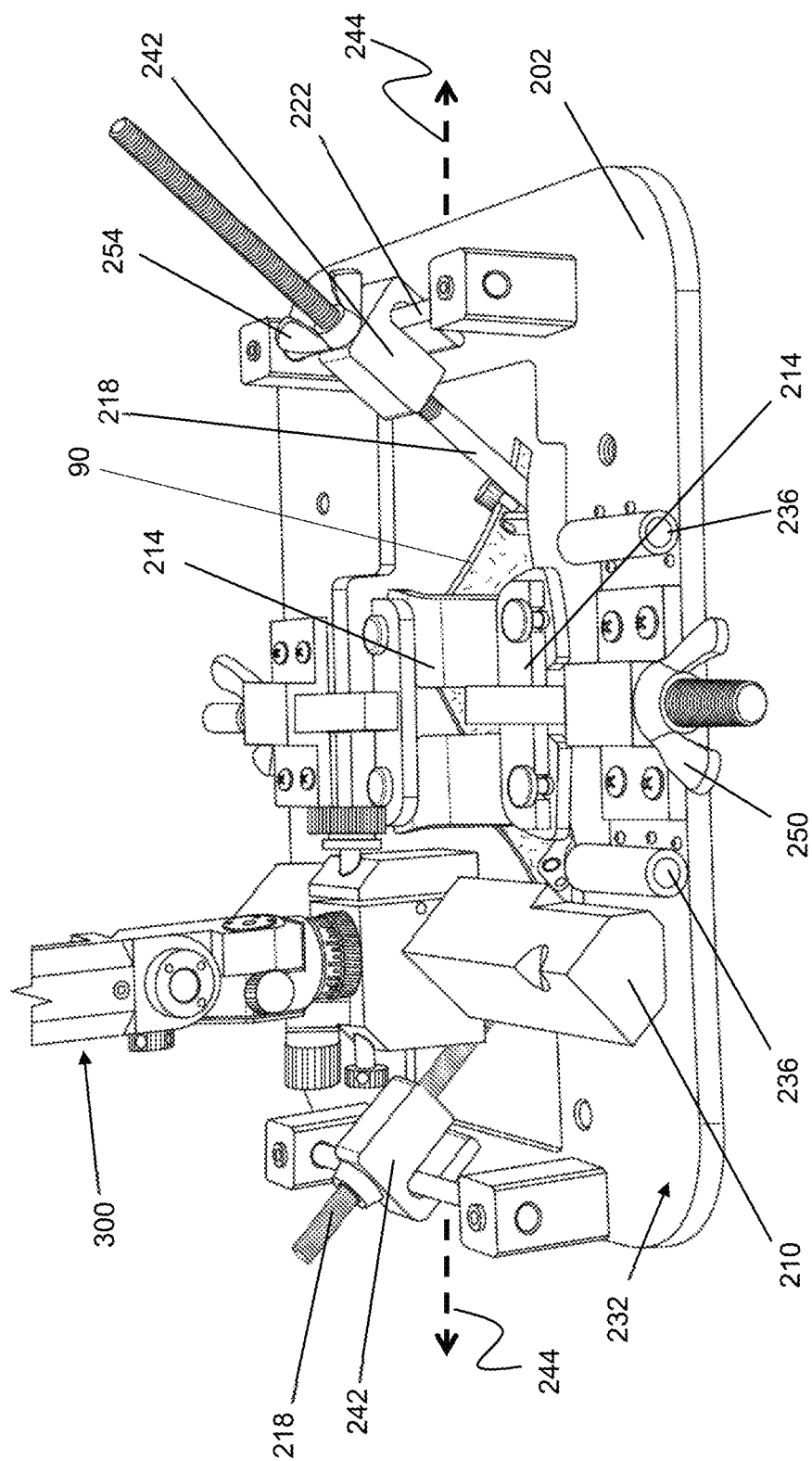
FIG. 3 is a pictorial diagram showing a perspective view of an exemplary embodiment of the subpial delivery system.
Figure 6:
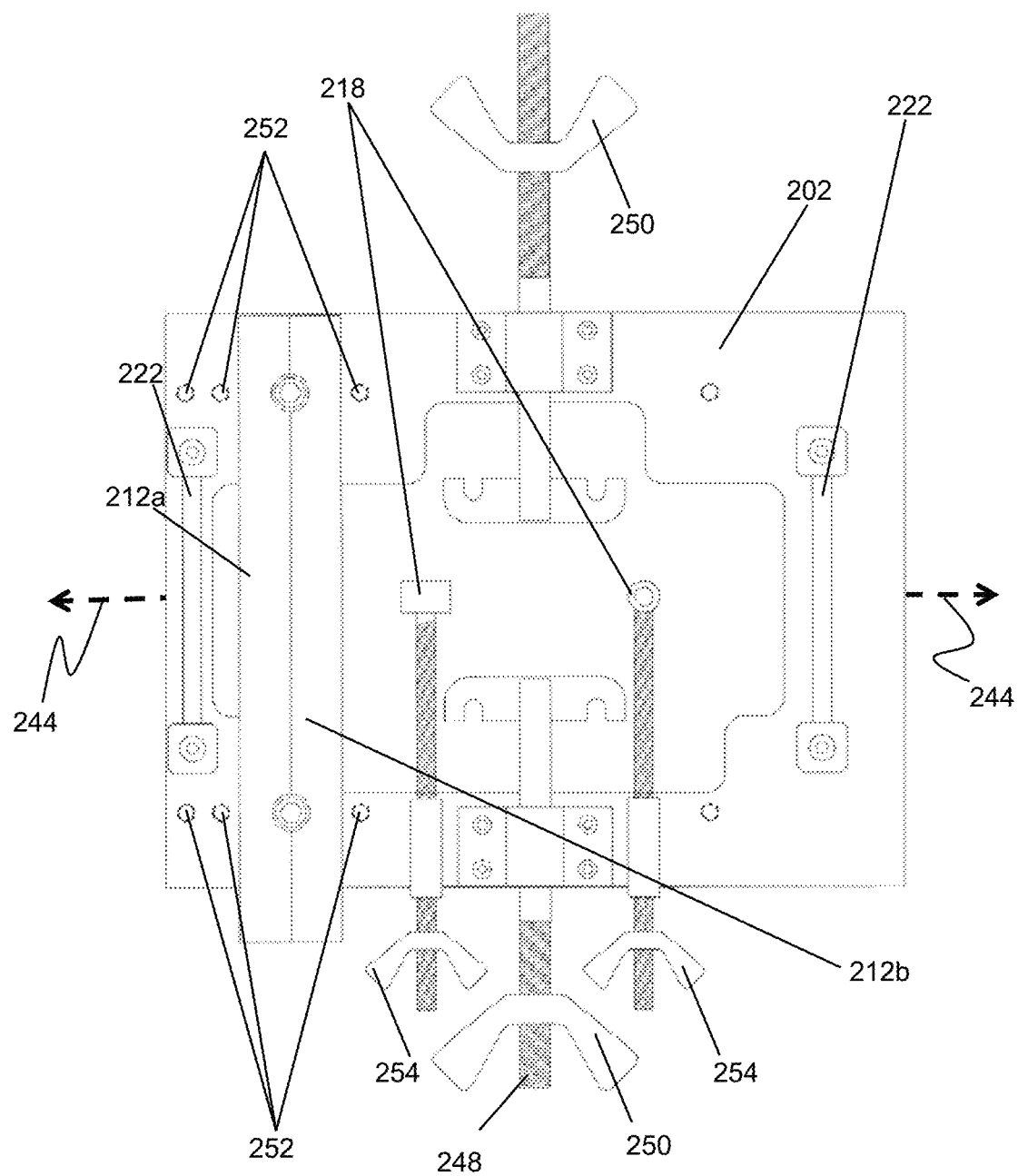
FIG. 6 is a pictorial diagram showing a top view of an exemplary embodiment of the platform of the subpial delivery system.

As shown in FIGS. 2, 3 and 6, anchor 218 may be fixedly attached to frame 202 via one or more bars 222, which are fixedly attached to top surface 232 of frame 202 and positioned perpendicular to axis 244 of frame 202. When so provided, each bar 222 may be located outside of the surgical site 90 defined by aperture 208. For example, a pair of bars 222 may be fixedly attached to top surface 232 of frame 202 in positions that are parallel to the position of the rail 210. Thus, each anchor 218 may be movably mounted to a respective bar 222 via a mount 242. For example, mount 242 of anchor 218 may be slidably disposed over bar 222 and fixed to bar 222 using a threaded nut.

Figure 4:
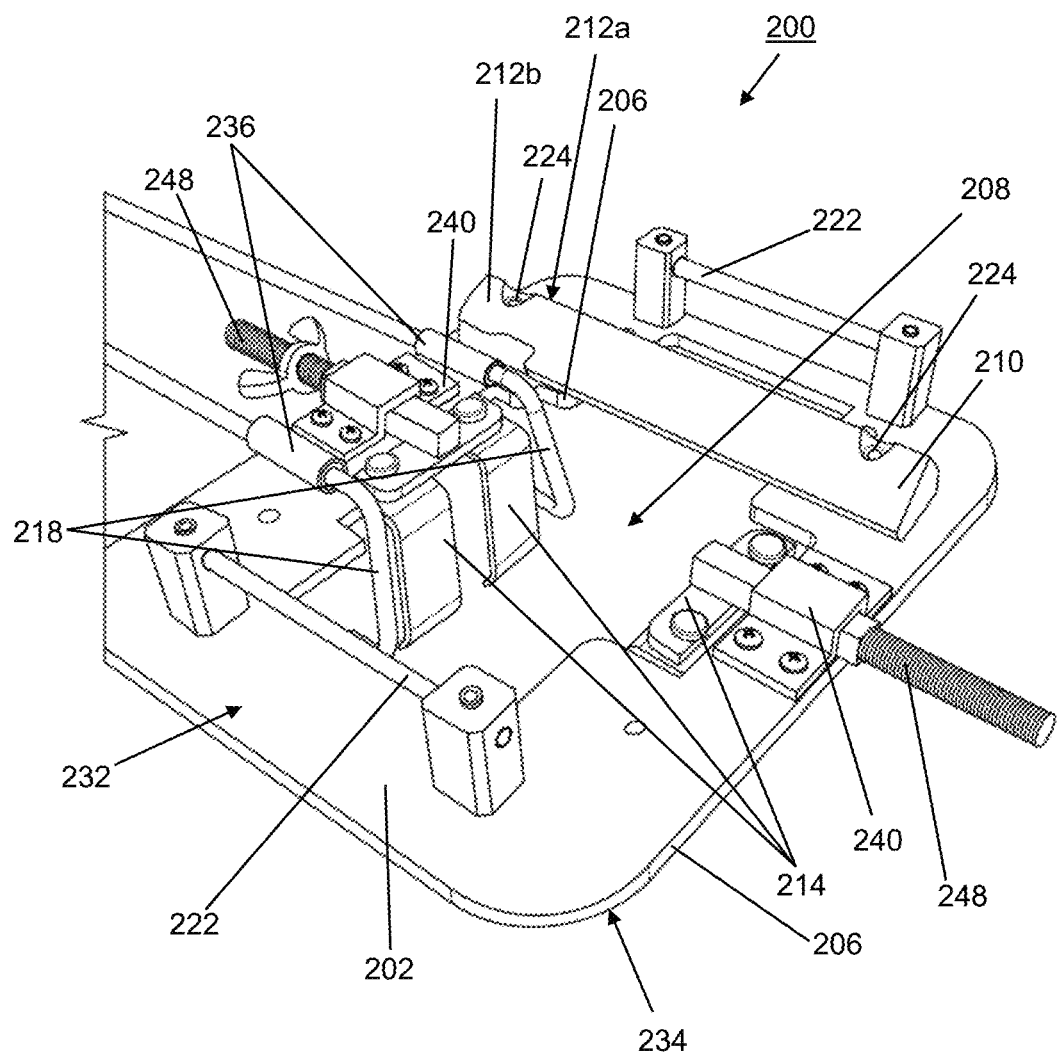
FIG. 4 is a pictorial diagram showing a perspective view of an exemplary embodiment of the platform of the subpial delivery system.

Turning now to FIGS. 3-5, there are shown various views of platform 200 in accordance with exemplary embodiments of the invention. As described herein, platform 200 may be referred to as "self-anchoring" in that it is configured to be secured over the surgical site of a subject. For example, platform 200 may incorporate one or more anchors 218 to engage a bone (e.g., the spinous process of a vertebra) within a surgical site so as to immobilize (i.e., anchor) and secure platform 200 over the surgical site. Thus, platform 200 provides firm and anchored attachment of subpial delivery system 100 to the spinal column of a subject over the surgical site following a complete or partial laminectomy. In various embodiments, platform 200 may be a reusable medical instrument designed to be cleaned and sterilized before each use. Platform 200 may thus be formed from, for example, stainless steel or titanium. In various embodiments, frame 202 includes an outer perimeter 204 and an inner perimeter 206, which defines aperture 208. As such, frame 202 may be formed in any of various shapes useful for performing the surgical procedure. For example, outer perimeter 204 and/or inner perimeter 206 of frame 202 may be rectangular, rounded rectangular, square, circular, stadium-shaped, polygonal, or any other shape.

As discussed above, rail 210 may be fixedly attached to top surface 232 of frame 202 and positioned perpendicular to axis 244 of frame 202. For example, rail 210 may be attached to frame 202 using screws 224, which may be threaded through holes disposed in opposing ends of rail 210. Thus, frame 202 may include multiple pairs of pre-drilled holes 252 (as shown in FIG. 5) to enable rail 210 to be mounted in various positions on the top surface 232 of frame 202. As such, the mounting position of rail 210 between outer perimeter 204 and inner perimeter 206 of frame 202 may adjusted as required by the user and/or surgical procedure to be performed. While rail 210 is shown as being shaped as a triangular prism, it should be understood that rail 210 may be formed as any of various shapes so long as rail 210 provides a complementary surface to engage and abut rail-engaging surfaces of manipulator 300, as discussed further herein. In various embodiments, rail 210 may be formed from any suitable material, such as stainless steel.

As shown in FIGS. 6 and 7, manipulator 300 may be moveably attached to rail 210 of platform 200. In various embodiments, manipulator 300 includes a post 314 having a central axis 320, which extends in a direction perpendicular to the top surface 232 of the frame 202. Moveably attached to a distal portion 332 of post 314 is a crossmember 316, which is positioned parallel to the top surface 232 of frame 202 and extends over the surgical site 90. Moveably attached to the crossmember 316 is a coupler 318, the coupler 318 having a threaded portion 330 configured for removable attachment to needle assembly 450.

Figure 8:
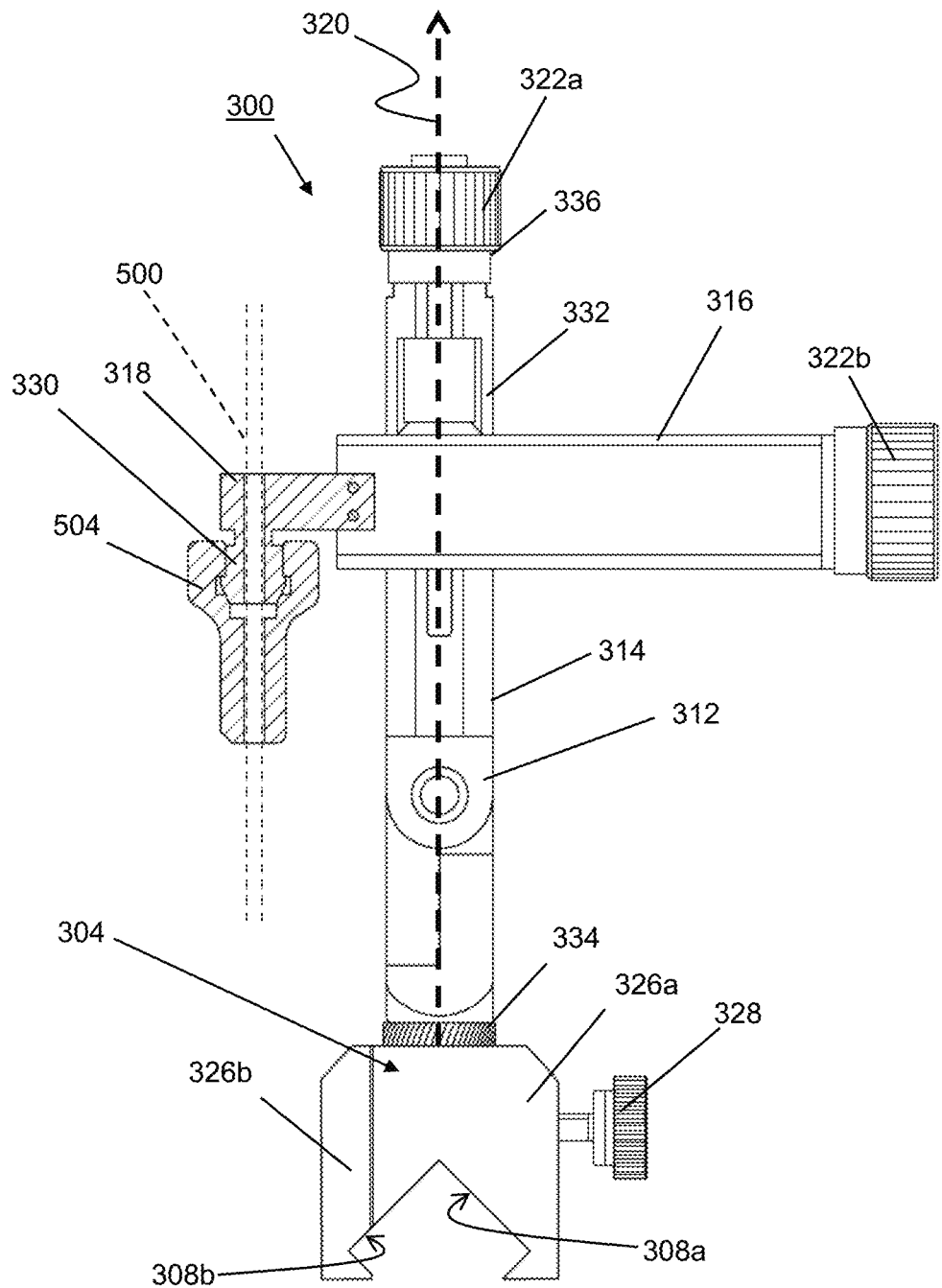
FIG. 8 is a pictorial diagram showing a side view of an exemplary manipulator of the subpial delivery system.
Figure 9:
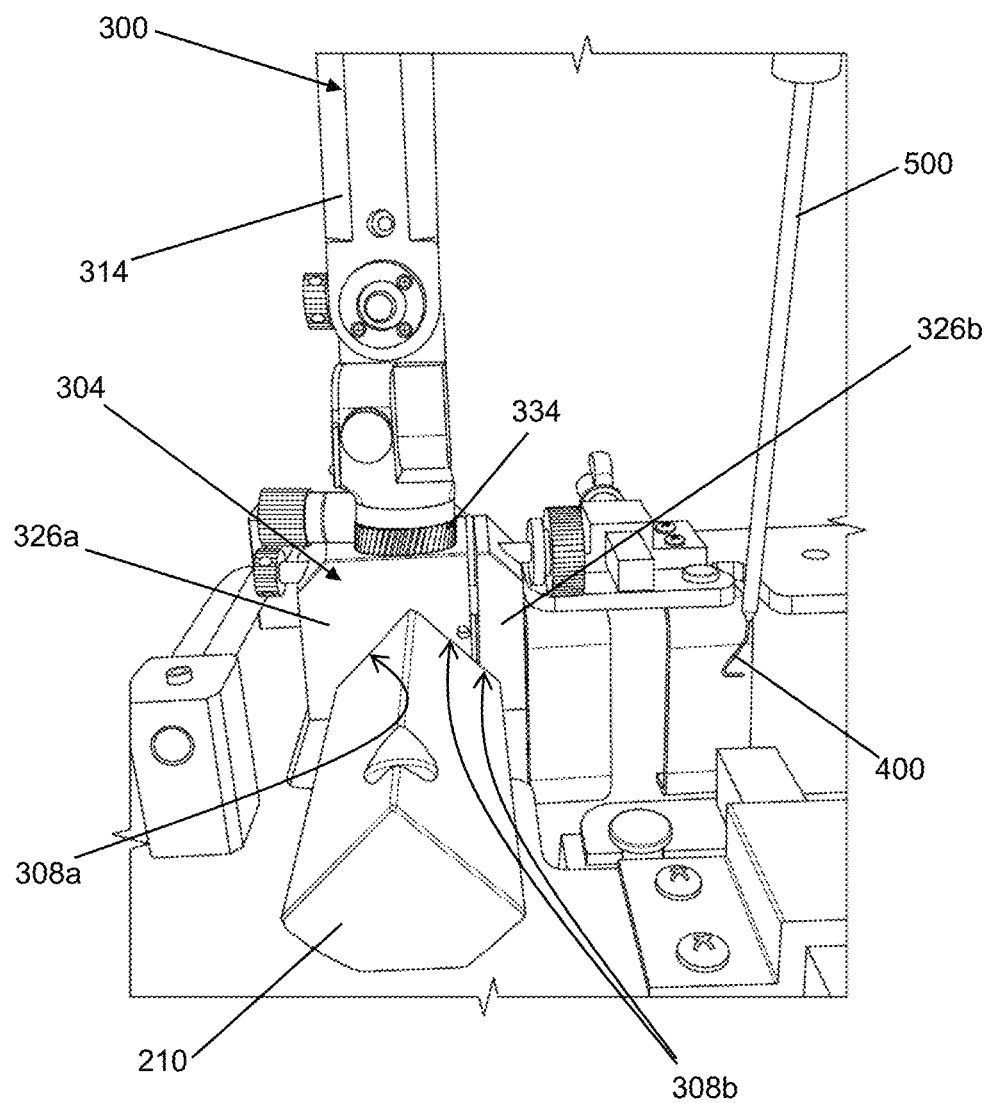
FIG. 9 is a pictorial diagram showing a partial perspective view of an exemplary manipulator attached to the rail of the platform of the subpial delivery system.
Figure 10:
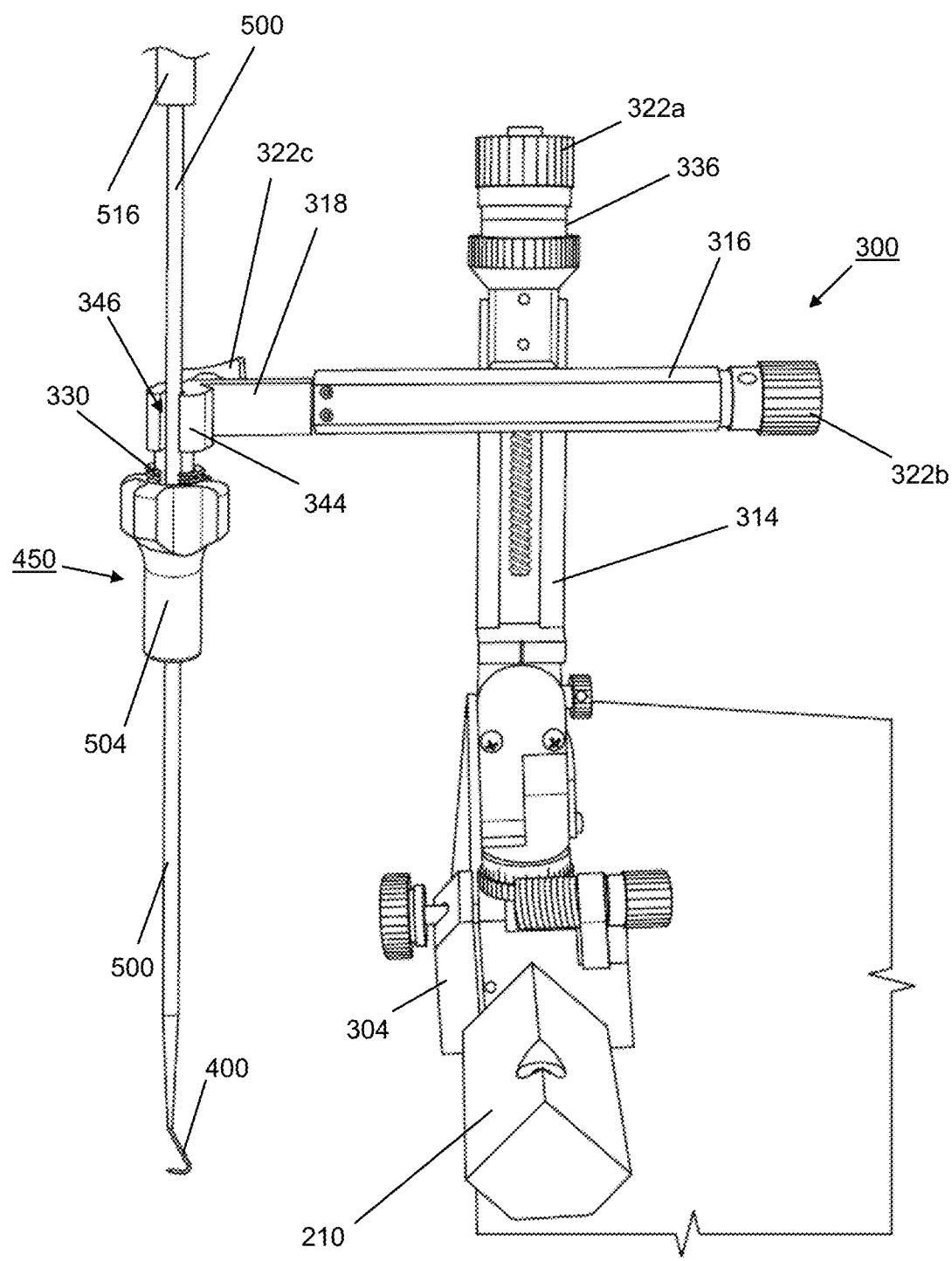
FIG. 10 is a pictorial diagram showing a perspective view of an exemplary needle assembly attached to the manipulator of the subpial delivery system.
Figure 11:
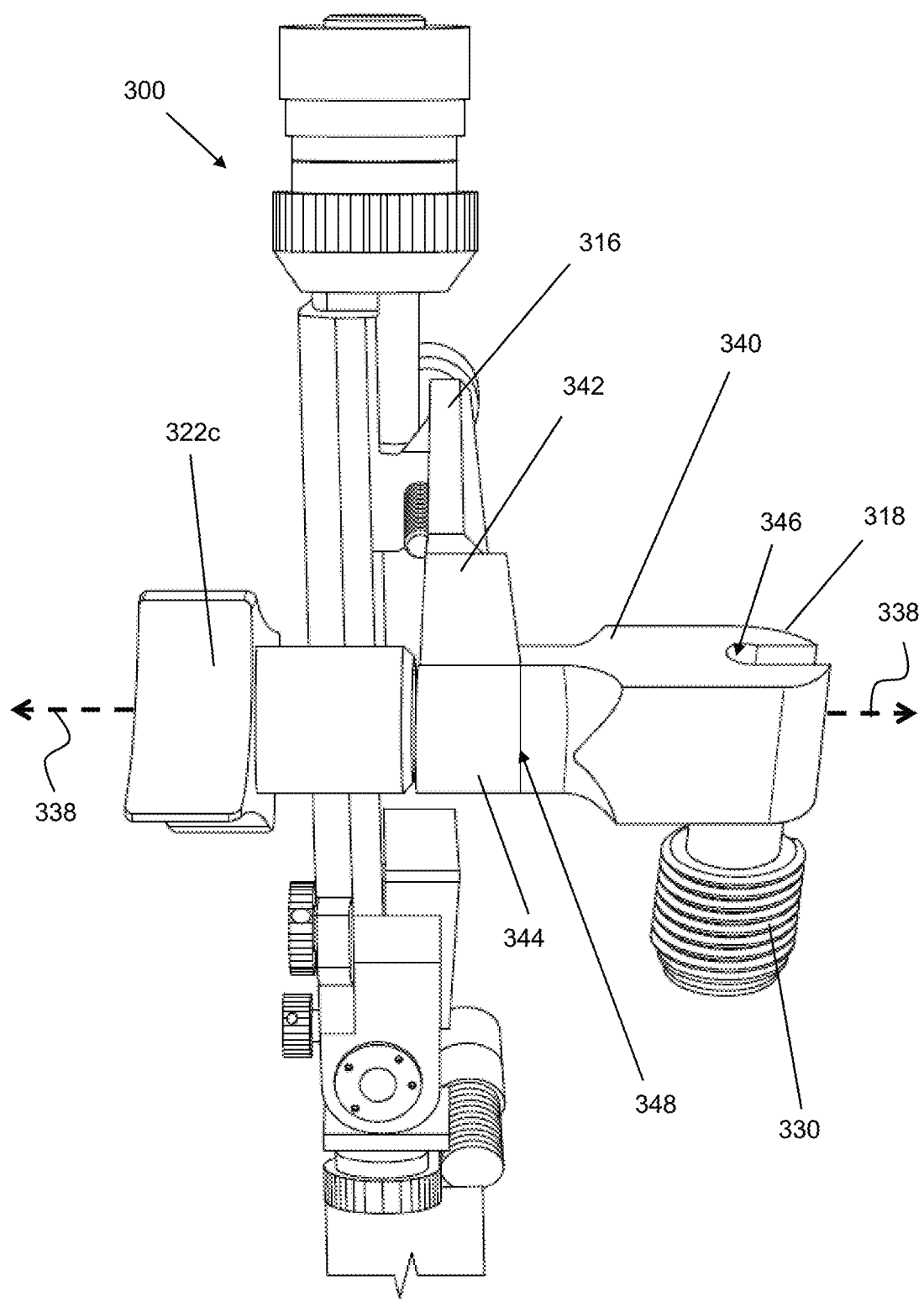
FIG. 11 is a pictorial diagram showing a perspective view of an exemplary coupler of the manipulator of the subpial delivery system.
Figure 12:
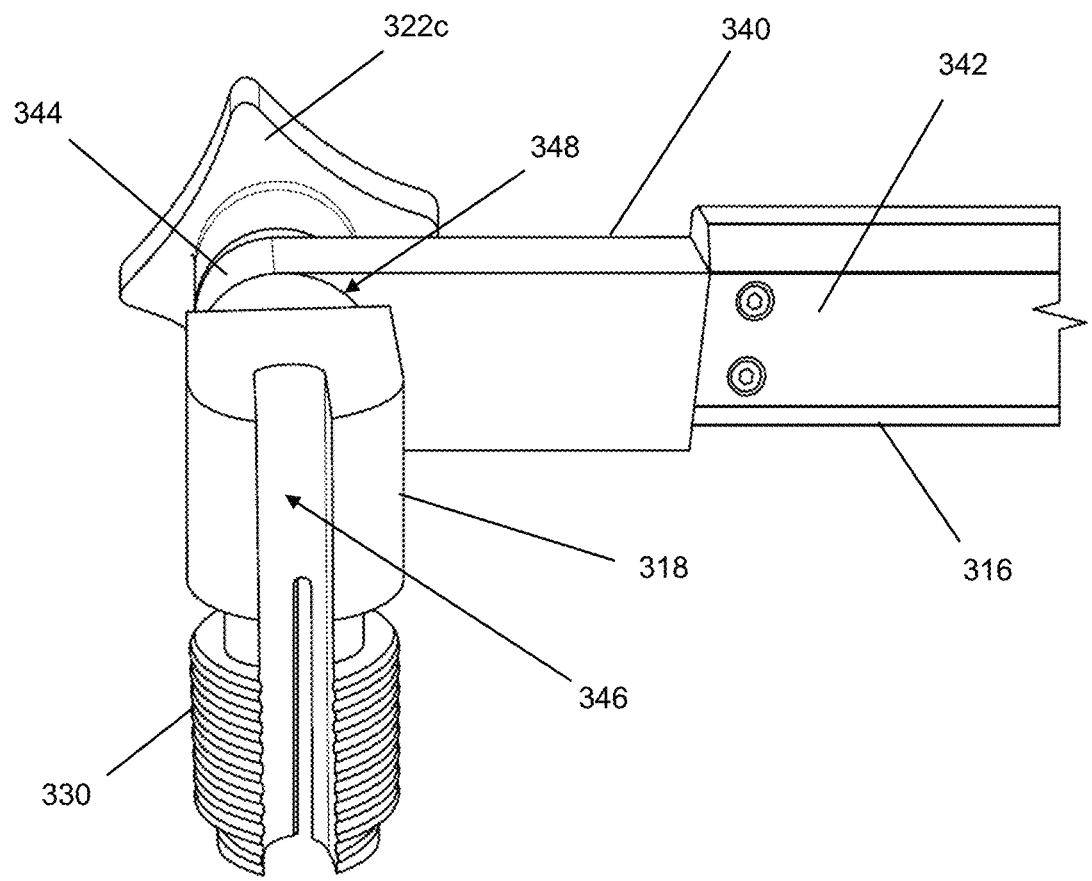
FIG. 12 is a pictorial diagram showing another perspective view of an exemplary coupler of the manipulator of the subpial delivery system.
Figure 13:
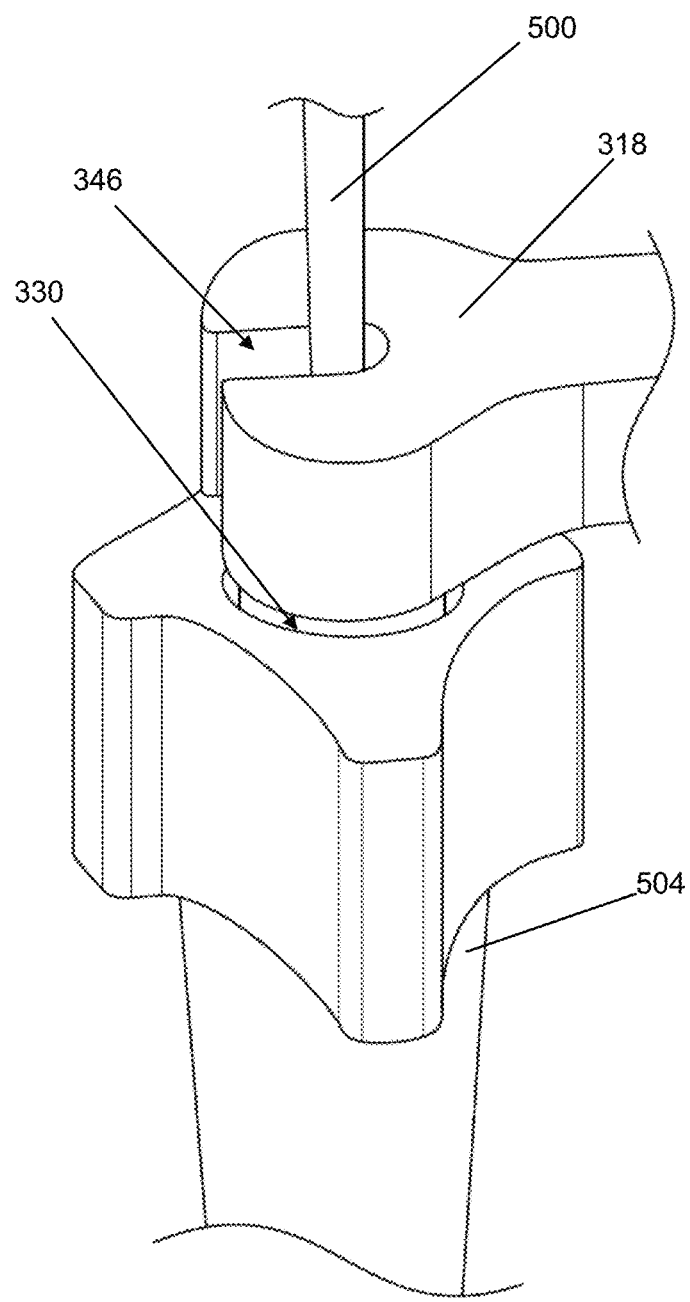
FIG. 13 is a pictorial diagram showing a partial perspective view of an exemplary needle assembly fixedly attached to the coupler of the subpial delivery system.

As shown in FIGS. 8-10, manipulator 300 may include a base 304 disposed at a proximal end 334 of post 314, the base 304 being configured for frictional attachment to rail 210 of frame 202. Thus, base 304 may include one or more vise jaws (326a and 326b), each having corresponding rail-engaging surfaces (308a and 308b), which are shaped to complement rail surfaces (212a and 212b). In an exemplary embodiment, base 304 also includes a base screw 328 configured for advancing jaw 326b toward opposing jaw 326a until rail-engaging surfaces (308a and 308b) of base 304 abut complementary rail surfaces (212a and 212b), respectively, thereby providing frictional attachment of manipulator 300 to platform 200.

As shown in FIGS. 8-11, manipulator 300 may further include a pivotal joint 312 disposed along post 314. Pivotal joint 312 may be configured to provide pivotal adjustment of the proximal end 336 of post 314 such that the central axis 320 of post 314 is no longer parallel to axis 244 of frame 202 (i.e., the proximal end 336 of post 314 may be pivoted in a direction away from central axis 320 thereof). In various embodiments, post 314 may further include a rotational adjustment such that the position of crossmember 316 may be varied relative to the incision of the surgical site 90, as desired by a user. In various embodiments, manipulator 300 includes a knob 322a disposed at a distal end 332 of post 314 that is configured to lock pivotal joint 312 of post 314 into a preselected position. Likewise, crossmember 316 may further a knob 322b that is configured to lock coupler 318 in a preselected position. Though described as rotatable knobs herein, as understood by one skilled in the art, other control mechanisms may be used instead of knobs, for example, ratcheting mechanisms, sliders, screws, etc.

As shown in FIGS. 8 and 10-12, coupler 318 includes an arm 340 having a first end 342 moveably attached to crossmember 316 and a second end 344 having a threaded portion 330. Threaded portion 330 of coupler 318 includes a slot 346 disposed therein that traverses through second end 344 in a direction parallel to central axis 320 of post 314. Slot 346 is configured to accept the elongated body 500 of needle assembly 450, as described below. In various embodiments, second end 344 of coupler 318 is crescent-shaped and may further include a rotatable joint 348 to allow for positional adjustment of the needle assembly relative to the surgical site 90. Thus, coupler 318 may further include a knob 322c that is configured to lock coupler 318 in a preselected position. For example, upon a first actuation of knob 322c, coupler 318 may be freely rotated about an axis 338 of coupler 318. Upon a second actuation, coupler may be fixed in a desired position such that needle 400 may be secured in a desired position relative to surgical site 90. In various embodiments, arm 340 may be straight, as shown in FIGS. 1 and 6. However, as shown in FIGS. 8-11, arm 340 of coupler 318 may include a right-angle bend between first end 342 and second end 344, in accordance with various embodiments of the disclosure. The bend of arm 340 permits a clear line of sight for a user (i.e., surgeon) to the surgical site 90 and allows for rotation of second end 344.

As shown in FIGS. 13-16, needle assembly 450 includes an elongated body 500 having an axis 512 and a first lumen 514 disposed therethrough. Elongated body 500 may therefore be inserted into slot 346 of coupler 318 and fastened to the manipulator 300 using a fastener 504 disposed at a distal end portion 506 of elongated body 500. Thus, fastener 504 may be rotated and advanced over threaded portion 330 until elongated body 500 is fixedly attached and secured to coupler 318 (see FIG. 13).

Figures 14A, 14B:
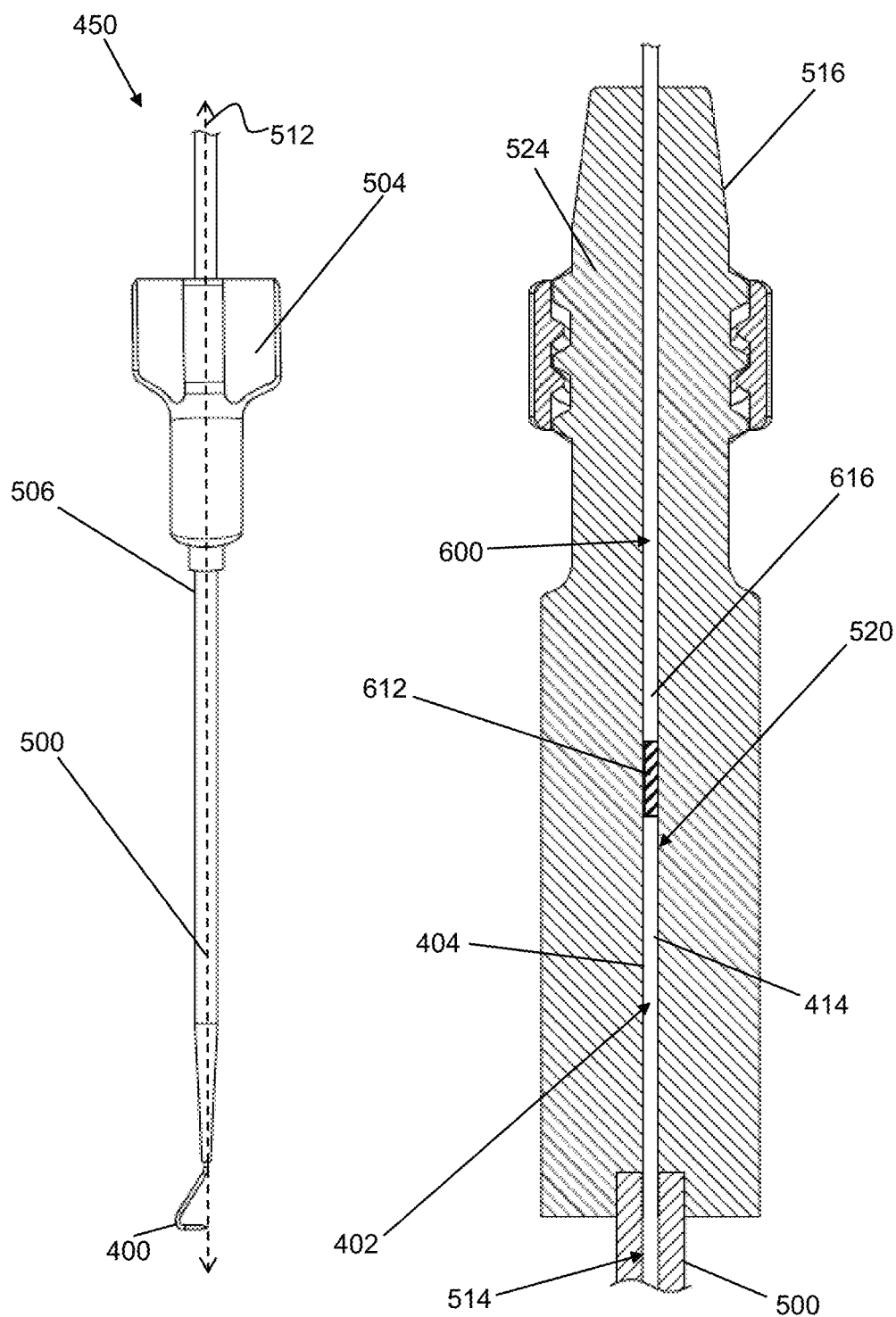
FIGS. 14A and 14B are pictorial diagrams showing a perspective view of an exemplary needle assembly (FIG. 14A) and a cross-sectional view of the fluid fitting of an exemplary embodiment of the needle assembly.
Figure 15:
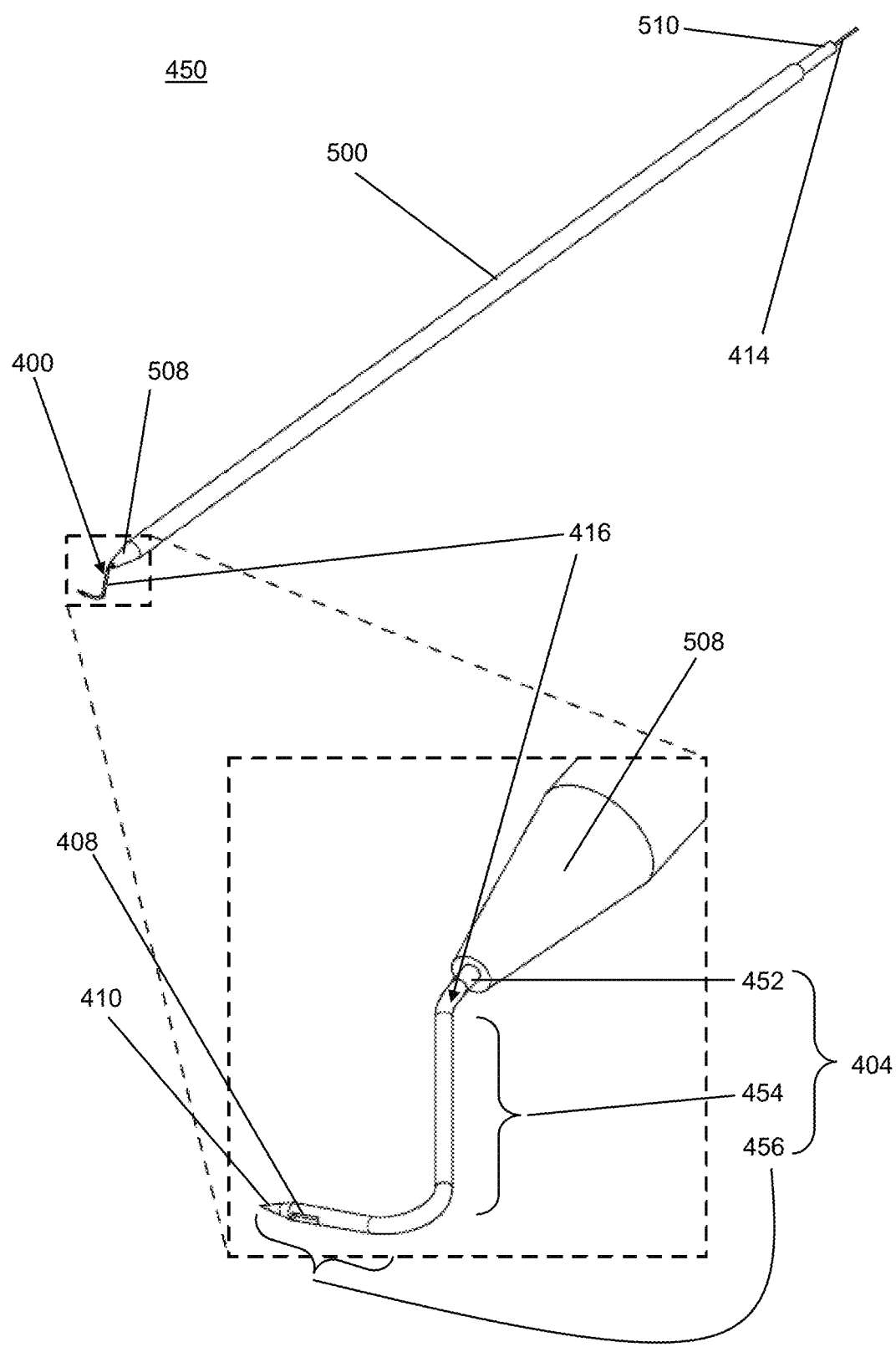
FIG. 15 is a pictorial diagram showing a perspective view of an exemplary needle assembly of the subpial delivery system.

As shown in FIG. 14, disposed within first lumen 514 of the elongated body 500 is an elongated shaft 404 of a needle 400, the elongated shaft 404 defining a second lumen 402. Elongated shaft 404 includes a distal end 414 and a proximal end portion 416. Provided at the proximal end portion 416 of the elongated shaft 404 of needle 400 is an upper section 452 substantially parallel to the axis 512 of the elongated body 500, a middle section 454 angled away from the axis 512 of the elongated body 500, and a lower section 456 angled toward the axis 512 of the elongated body 500, such that the lower section is substantially perpendicular to the axis 512 of the elongated body 500. As shown in FIGS. 15-16, disposed at the proximal end 414 of the elongated shaft 404 is a point 410 such that point 410 is positioned in alignment with the axis 512 of the elongated body 500. Disposed within the lower section 456 of elongated shaft 404 is an opening 408 that is in fluid communication with the second lumen 402. In various embodiments, needle assembly 450 includes a fastener 504 disposed on a distal end portion 506 of elongated body 500. Fastener 504 may be being configured to engage threaded portion 330 of coupler 318 to secure the elongated body 500 of the needle assembly 450 to manipulator 300.

In various embodiments, needle 400 may be bent or curved so that lower section 456 is substantially parallel to the spine of a subject to facilitate insertion of the needle into the subpial space while avoiding sensitive structures such as blood vessels and dorsal root fibers (e.g., nerves). In various embodiments, the opening 408 of needle 400 is proximate to the dorsal surface of the spinal cord, for example, opening 408 may be a side port. Needle 400 is thus designed for accuracy and precision in reaching targeted spinal subpial locations without damaging surrounding tissue and nerves. Moreover, the accuracy and precision of positioning point/tip 410 of needle 400 at the targeted subpial space is critical in delivering therapeutic vectors into unilateral dorsal horn neurons of selected spinal cord segments. In exemplary embodiments, needle 400 may be formed from a 23-35-gauge stainless steel tube. As such, approximately 1-4 mm of the tip is bent at about 40°-50° to form the lower section 456 thereof and sharpened using a fine beveler system.

Figure 17:
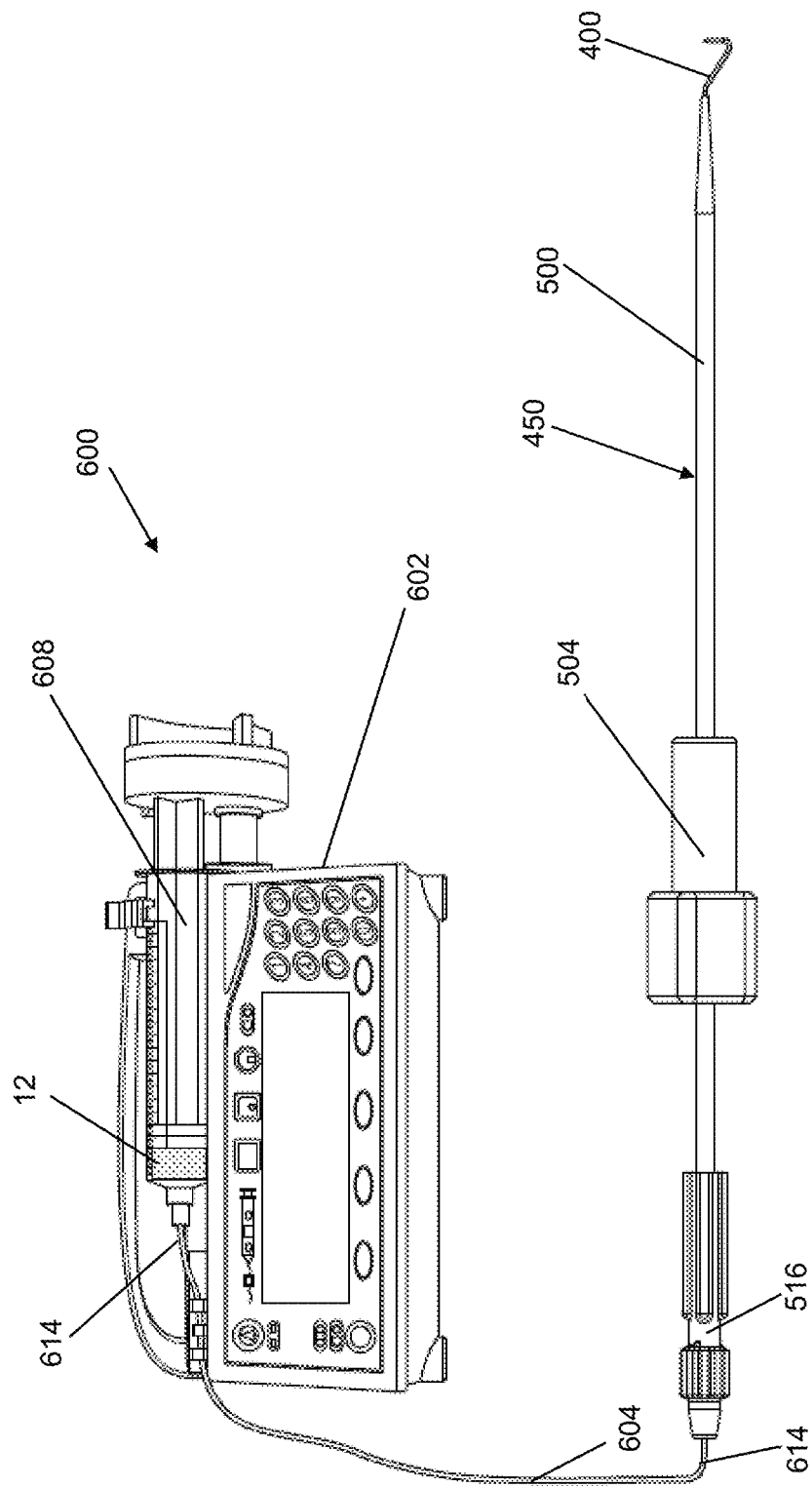
FIG. 17 is a pictorial diagram showing a front plan view diagram of an exemplary microinjector connected to the reservoir of the subpial delivery system.

Reservoir 600 is fixedly attached to a distal end 510 of elongated body 500 of needle assembly 450 and disposed in fluid communication with the second lumen 402 of the elongated shaft 404 of needle 400. Thus, reservoir 600 may be configured to contain a substrate prior to delivery of the substrate through opening 408 of needle 400. In one or more embodiments, needle assembly 450 includes a fluid fitting 516 disposed at distal end portion 506 of elongated body 500 and configured to provide removable attachment between needle assembly 450 and reservoir 600, as shown in FIGS. 16 and 17. In various embodiments, needle assembly 450 may further include a fluid fitting 516 disposed at a distal end 506 thereof. Fluid fitting 516 may include a body 524 having a lumen 520 sized and shaped to accept distal end 414 of elongated shaft 404 of needle 400 (see FIG. 13). In various embodiments, distal end 414 of elongated shaft 404 and a proximal end 616 of reservoir 600 may be separated by a space 612 within fluid fitting 516.

In various embodiments, reservoir 600 may be formed from tubing, such as surgical tubing 604. Reservoir 600 may further include a syringe 608 disposed at a distal end 614 of tubing 604, the syringe 608 being configured to supply the substrate 12 to reservoir 600. In various embodiments, reservoir 600 may further include a pump, such as microinjector 602, attached to tubing 604, the pump being configured to pump the substrate from reservoir 600 through opening 408 of needle 400 (see FIG. 17). Microinjector 602 may be a digital microinjector (e.g., Medfusion 3500 Syringe Pump) and may be used to load and administer continuous or discrete amounts of the substrate into the, for example, spinal subpial space through needle 400. In various embodiments, reservoir 600 may be a bag (not shown) disposed at a distal end 614 of tubing 604, the bag containing the substrate to be administered to the subpial space of the subject. Substrate 12 may be selected from the group consisting of soluble substances, cells, vectors, drugs, viruses, plasmids, and growth factors.

Accordingly, manipulator 300 is designed to allow a user to precisely place needle 400 into, for example, a spinal subpial space of a subject. Manipulator 300 may therefore be a reusable medical device that is cleaned and sterilized before each use. While the body may be made from any rigid material, in certain embodiments, the manipulator may be made from any non-corrosive metal, such as stainless steel.

As shown in FIGS. 18-21, an exemplary use of subpial delivery system 100 is as follows. The subject is positioned in a prone position and subject to anesthesia suitable for the surgical procedure. A standard posterior approach is performed, targeting T1 to T10 of the spinal cord, followed by an "open door" laminoplasty, leaving the dura mater intact. Sterile saline may be used to clean/flush the operatory wound (i.e., surgical site 90), and sterile fields may be applied to protect the subject. Platform 200 is prepared for the procedure and placed over the incision. Anchors 218 are used to engage one or more bones (e.g., spinous process) within the surgical site 90 to fix the platform 200 in place. Manipulator 300 is attached to frame 202 of platform 200 above the surgical site of the subject and adjusted as necessary.

The fluid fitting 516 of the needle assembly 450 is opened and the reservoir 600 is filled with substrate 12. Thereafter, the fluid fitting 516 is reconnected, thereby establishing fluid communication between the reservoir 600 and the needle assembly 450. The elongated shaft 500 of needle assembly 450 is inserted into slot 346 of coupler 318 and advancing fastener 504 over threaded portion 330. Post 314 may be rotated about or angled relative to axis 320, crossmember 316 may be adjusted toward or away from surgical site 90 along axis 320, and coupler may be rotated. For example, crossmember 316 may be lowered along post 314 so that needle 400 is lowered closer to the exposed spinal cord surface. The tubing 604 of the reservoir 600 is run through a digital microinjector 602, if present, which is operated to remove any air in the lines (i.e., the needled assembly 450 is primed). Needle 400 is thereafter lowered into the spinal cord parenchyma, avoiding damage to blood vessels under visual guidance, to open the pia (and advance the needle 400 into the subpial space). In various embodiments, the needle assembly 450 may be adjusted using manipulator 300 prior to inserting point 410 of needle 400 such that lower length 456 is substantially parallel to spinal cord 39 of the subject 30. Digital microinjector 602 (if present) is then activated to deliver a dose of substrate 12 to the subpial space of the spinal cord. In an exemplary embodiment, soluble substances, vectors, or cells may be injected into spinal subpial space at rate between 0.1-5 microliters (µl) per minute. After retracting needle 400, needle 400 may be repositioned for repeated injection steps, as necessary. Following completion of all injections, needle 400 is retracted and manipulator 300 may be removed from platform 200.

A dural closure is performed, followed by a laminary closure. Each of the anatomical layers (e.g., muscle, subcutaneous tissue, and skin) are then closed using resorbable materials. As such, vector or cell delivery by means of the subject system may be used to treat spinal traumatic injury, symptoms associated with amyotrophic lateral sclerosis (ALS), chronic pain, muscle spasticity, and multiple sclerosis.

The disclosure is not intended to limit the present invention to the precise forms or particular fields of use disclosed. It is contemplated that various alternate embodiments and/or modifications to the present invention, whether explicitly described or implied herein, are possible in light of the disclosure. For example, it is contemplated that the various embodiments set forth herein may be combined together and/or separated into additional embodiments where appropriate. Where applicable, the ordering of various steps described herein can be changed, combined into composite steps, and/or separated into sub-steps to provide features described herein.

Embodiments described above illustrate but do not limit the invention. It should be understood that numerous modifications and variations are possible in accordance with the principles of the present invention. Accordingly, the scope of the invention is defined only by the following claims.

What is claimed is:

1. A subpial delivery system comprising:
 (a) a platform comprising:
  (i) a frame having a top surface, a bottom surface, and an axis, the frame comprising an aperture defining a surgical site;
  (ii) a rail fixedly attached to the top surface of the frame and positioned perpendicular to the axis;
  (iii) a retractor moveably attached to the top surface of the frame and configured to move in a direction perpendicular to the axis; and
  (iv) an anchor moveably attached to the frame and configured to engage a bone within the surgical site so as to secure the platform over the surgical site;
 (b) a manipulator moveably attached to the rail of the platform, the manipulator comprising:
  (i) a post having a central axis and extending in a direction perpendicular to the top surface of the frame;
  (ii) a crossmember moveably attached to a distal portion of the post and positioned parallel to the top surface of the frame; and
  (iii) a coupler moveably attached to the crossmember, the coupler comprising a threaded portion configured for removable attachment to a needle assembly;
 (c) a needle assembly removably attached to the coupler, the needle assembly comprising:
  (i) an elongated body having an axis and a first lumen disposed therethrough;
  (ii) a fastener disposed on distal end portion of the elongated body, the fastener being configured to engage the threaded portion of the coupler; and
  (iii) a needle comprising:
   (a) an elongated shaft disposed within the first lumen of the elongated body, the elongated shaft defining a second lumen and having a proximal end portion comprising an upper section substantially parallel to the axis of the elongated body, a middle section angled away from the axis of the elongated body, and a lower section angled toward the axis of the elongated body, such that the lower section is substantially perpendicular to the axis of the elongated body;

(b) a point disposed at the proximal end of the elongated shaft such that the point is positioned in alignment with the axis of the elongated body; and (c) an opening disposed within the lower section, wherein the opening is in fluid communication with the second lumen; and (d) a reservoir fixedly attached to a distal end of the elongated body of the needle assembly and disposed in fluid communication with the second lumen, the reservoir being configured for containing a substrate prior to delivery of the substrate through the opening of the needle.

2. The subpial delivery system of claim 1, wherein the frame comprises a pair of retractors, each retractor being attached to the top surface of the frame at opposing sides of the surgical site.

3. The subpial delivery system of claim 1, wherein the frame comprises a pair of anchors, each anchor being attached to the frame at opposing sides of the surgical site.

4. The subpial delivery system of claim 3, wherein the frame further comprises a pair of bars fixedly attached to the top surface and positioned perpendicular to the axis of the frame, wherein each bar is located outside of the surgical site defined by the aperture, and wherein each anchor is movably mounted to each bar via a mount.

5. The subpial delivery system of claim 1, wherein the frame comprises a pair of anchors, each anchor being attached to the frame on the same side of the surgical site.

6. The subpial delivery system of claim 5, wherein the frame further comprises a pair of sleeves fixedly attached to the frame and configured for movable attachment to the anchors.

7. The subpial delivery system of claim 1, wherein the anchor comprises a pair of serrated jaws disposed at a proximal end of the anchor, the pair of serrated jaws being hingedly attached to one another and configured to clamp onto a bone within the surgical site.

8. The subpial delivery system of claim 1, wherein the anchor comprises a hook disposed at a proximal end, the hook being configured to engage a bone within the surgical site.

9. The subpial delivery system of claim 1, wherein the manipulator further comprises a base disposed at a proximal end of the post, the base being configured for frictional attachment to the rail of the frame.

10. The subpial delivery system of claim 1, wherein the manipulator further comprises a pivotal joint disposed along the post, the pivotal joint being configured to allow the distal portion of the post to pivot in a direction away from the central axis thereof.

11. The subpial delivery system of claim 10, wherein the manipulator further comprises a first knob disposed at a distal end of the post, the first knob being configured to lock the pivotal joint of the post in a preselected position.

12. The subpial delivery system of claim 11, wherein the crossmember further comprises a second knob, the second knob being configured to lock the coupler in a preselected position.

13. The subpial delivery system of claim 1, wherein the coupler further comprises an arm having a first end slidingly disposed within the crossmember and the threaded portion disposed at a second end, and a slot disposed in the threaded portion and traversing the second end of the coupler, the slot being configured to accept the elongated body of the needle assembly.

14. The subpial delivery system of claim 13, wherein the arm further comprises a rotatable joint configured to adjust the angle of the slot and threaded portion relative to the central axis of the post.

15. The subpial delivery system of claim 14, wherein the arm further comprises a knob configured to lock the rotatable joint in a preselected position.

16. The subpial delivery system of claim 1, wherein the opening of the needle is located in a position facing toward the surgical site.

17. The subpial delivery system of claim 1, wherein the needle assembly further comprises a fluid fitting disposed at a distal end of the elongated body and configured to provide removable attachment between the needle assembly and the reservoir.

18. The subpial delivery system of claim 17, wherein the fluid fitting comprises a body having a lumen sized and shaped to accept the distal end of the elongated shaft of the needle, wherein the distal end of the elongated shaft and the proximal end of the reservoir are separated by a space.

19. The subpial delivery system of claim 1, wherein the reservoir is formed from tubing.

20. The subpial delivery system of claim 19, wherein the reservoir further comprises a syringe disposed at a distal end of the tubing and configured to supply the substrate to the reservoir.

21. The subpial delivery system of claim 19, further comprising a pump attached to the tubing, the pump being configured to pump the substrate from the reservoir through the opening of the needle.

22. The subpial delivery system of claim 1, wherein the substrate is selected from the group consisting of soluble substances, cells, vectors, drugs, viruses, plasmids, and growth factors.

23. A method of delivering a substrate to a subpial space of a subject comprising:

(a) exposing a spinal cord of the subject;

(b) positioning and securing the subpial delivery system of claim 1 over the exposed spinal cord thereby creating a surgical site;

(c) loading a substrate to be delivered to the subpial space into the reservoir;

(d) inserting the point of the needle into subpial space of the spinal cord in a direction substantially parallel to the spinal cord, thereby creating a pial opening site of the subpial space; and (e) delivering a dose of the substrate to the spinal cord.

24. The method of claim 23, further comprising adjusting the needle assembly using the manipulator prior to the step of inserting such that the lower section is substantially parallel to the spinal cord of the subject.

25. The method of claim 23, wherein the step of loading comprises:

(a) disconnecting a fluid fitting disposed at a distal end of the elongated body of the needle assembly;

(b) flowing the substrate into the reservoir; and (c) reconnecting the reservoir to the needle assembly.

26. The method of claim 25, further comprising priming the subpial delivery system prior to the step of inserting by flowing substrate from the reservoir through the opening of the needle.

27. The method of claim 23, wherein the step of delivering comprises activating a pump attached to the reservoir, the pump being configured to control flow of the substrate of the reservoir through the opening of the needle.

28. The method of claim 23, wherein the step of delivering comprises actuating a syringe attached to a distal end of the reservoir, the syringe being configured to control flow of the substrate of the reservoir through the opening of the needle.

29. The method of claim 23, further comprising performing a laminectomy on the subject prior to the step of positioning and securing.

\* \* \* \* \*